US009081632B2

(12) United States Patent
Arms et al.

(10) Patent No.: US 9,081,632 B2
(45) Date of Patent: Jul. 14, 2015

(54) COLLABORATION METHODS FOR NON-PROGRAMMATIC INTEGRATION SYSTEMS

(75) Inventors: Randall Arms, Weatherby Lake, MO (US); Brian G Anderson, Overland Park, KS (US); Scott Coons, Lawrence, KS (US)

(73) Assignee: Lexmark International Technology SA (CH)

( * ) Notice: Subject to any disclaimer, the term of this patent is extended or adjusted under 35 U.S.C. 154(b) by 319 days.

(21) Appl. No.: 13/091,646

(22) Filed: Apr. 21, 2011

(65) Prior Publication Data

US 2012/0102118 A1    Apr. 26, 2012

Related U.S. Application Data

(60) Provisional application No. 61/326,655, filed on Apr. 21, 2010.

(51) Int. Cl.

| | |
|---|---|
| *G06F 15/16* | (2006.01) |
| *G06F 9/54* | (2006.01) |
| *G06Q 10/10* | (2012.01) |
| *G06Q 50/22* | (2012.01) |

(52) U.S. Cl.
CPC .............. *G06F 9/542* (2013.01); *G06Q 10/109* (2013.01); *G06Q 10/1095* (2013.01); *G06Q 50/22* (2013.01)

(58) Field of Classification Search
USPC ................................................ 709/204–207
See application file for complete search history.

(56) References Cited

U.S. PATENT DOCUMENTS

| | | | |
|---|---|---|---|
| 6,128,624 A | 10/2000 | Papierniak et al. | |
| 6,334,158 B1 | 12/2001 | Jennyc et al. | |
| 6,542,740 B1 | 4/2003 | Olgaard et al. | |
| 6,651,168 B1 | 11/2003 | Kao et al. | |
| 7,568,219 B2 | 7/2009 | Campbell et al. | |
| 7,599,985 B2 | 10/2009 | Doyle et al. | |
| 8,141,140 B2 | 3/2012 | Wenzel et al. | |
| 8,539,568 B1 | 9/2013 | Milas | |
| 2001/0032257 A1 * | 10/2001 | Wells et al. ................... | 709/223 |
| 2002/0138446 A1 | 9/2002 | Antonin et al. | |
| 2002/0184325 A1 * | 12/2002 | Killcommons et al. ...... | 709/206 |
| 2004/0003353 A1 | 1/2004 | Rivera et al. | |
| 2004/0044987 A1 | 3/2004 | Kompalli et al. | |
| 2004/0107118 A1 | 6/2004 | Harnsberger et al. | |
| 2004/0255289 A1 | 12/2004 | George et al. | |
| 2005/0278270 A1 | 12/2005 | Carr et al. | |
| 2006/0047682 A1 | 3/2006 | Black et al. | |
| 2006/0117067 A1 | 6/2006 | Wright et al. | |

(Continued)

*Primary Examiner* — Brian J Gillis
*Assistant Examiner* — Michael A Keller

(57) ABSTRACT

Methods and systems for collaborating when one or more other users view or access the same, similar, or otherwise data. The collaboration method includes automatically non-programmatically collecting application data from a first mapped location of a mapped source reference of an application used by a first user and automatically non-programmatically collecting application data from a second mapped location of a mapped source reference of an application used by a second user. The integration application determines whether the collected application data from the first mapped location matches the collected application data from the second mapped location, and if the first collected application data matches the second collected application data, that integration application automatically notifies at least one of the first user and second user. The match determination may occur when the users are simultaneously accessing the data or at different times.

20 Claims, 15 Drawing Sheets

(56) References Cited

U.S. PATENT DOCUMENTS

| | | |
|---|---|---|
| 2006/0167929 A1 | 7/2006 | Chakraborty et al. |
| 2006/0200387 A1* | 9/2006 | Saini ................................ 705/26 |
| 2007/0204029 A1 | 8/2007 | Igarashi et al. |
| 2008/0091780 A1* | 4/2008 | Balan et al. .................... 709/204 |
| 2008/0120375 A1* | 5/2008 | Levy .............................. 709/204 |
| 2008/0178304 A1 | 7/2008 | Jeansonne et al. |
| 2008/0215892 A1 | 9/2008 | Lindinger et al. |
| 2008/0263469 A1 | 10/2008 | Nasle et al. |
| 2009/0106558 A1 | 4/2009 | Delgrosso et al. |
| 2009/0119255 A1 | 5/2009 | Frank et al. |
| 2009/0138826 A1 | 5/2009 | Barros |
| 2009/0271653 A1 | 10/2009 | Zhu et al. |
| 2009/0299914 A1* | 12/2009 | Moran et al. ................. 705/36 R |
| 2009/0300773 A1 | 12/2009 | Pal |
| 2010/0010968 A1 | 1/2010 | Redlich et al. |
| 2010/0011337 A1 | 1/2010 | Young et al. |
| 2010/0070448 A1 | 3/2010 | Omoigui |
| 2010/0070500 A1 | 3/2010 | Cui et al. |
| 2010/0122178 A1 | 5/2010 | Konig et al. |
| 2010/0153836 A1 | 6/2010 | Krassner et al. |
| 2010/0179854 A1* | 7/2010 | Shafer et al. ...................... 705/9 |
| 2010/0223551 A1 | 9/2010 | Twig et al. |
| 2010/0228693 A1 | 9/2010 | Dawson et al. |
| 2010/0318486 A1* | 12/2010 | Stafford et al. ................. 706/47 |
| 2010/0318892 A1 | 12/2010 | Teevan et al. |
| 2011/0046970 A1* | 2/2011 | Fontenot .......................... 705/2 |
| 2011/0258001 A1 | 10/2011 | Green et al. |
| 2012/0284617 A1 | 11/2012 | Nouard et al. |

* cited by examiner

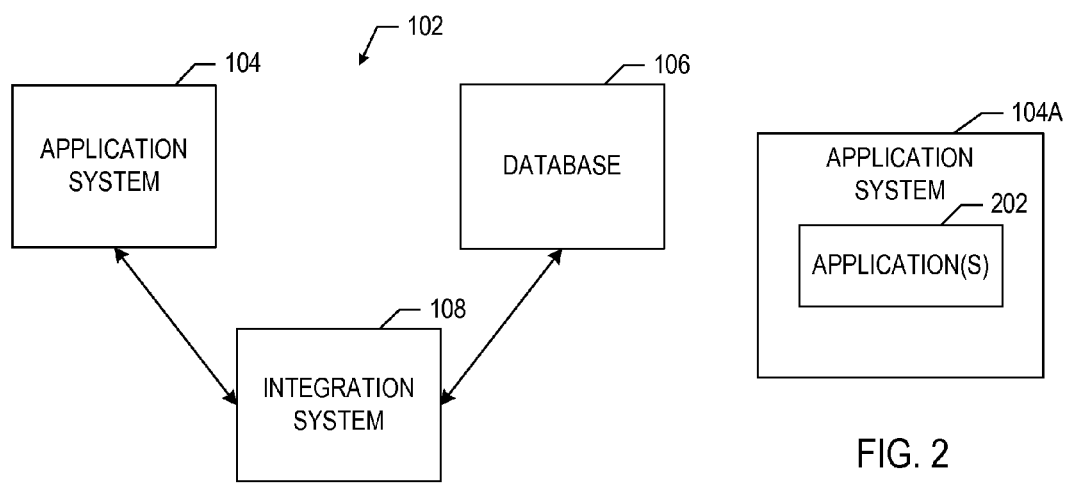
FIG. 1
FIG. 2
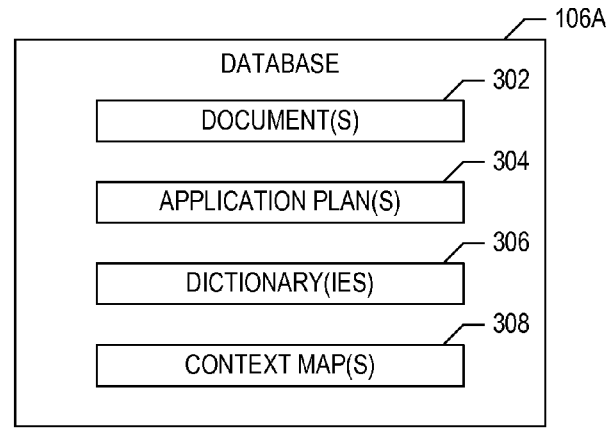
FIG. 3

COLLABORATION METHODS FOR NON-PROGRAMMATIC INTEGRATION SYSTEMS

CROSS REFERENCES TO RELATED APPLICATIONS

Pursuant to 35 U.S.C. 119, the present application is related to and claims benefit from U.S. patent application No. 61/326,655, filed Apr. 21, 2010, entitled "Collaboration Non-Programmatic Integration System," the content of which is hereby incorporated by reference herein in its entirety.

This application is related to U.S. patent application Ser. No. 13/091,617, entitled Synchronized Sign-On Methods for Non-Programmatic Integration Systems, filed on the same date as this application, U.S. patent application Ser. No. 13/091,661, entitled Notification Methods for Non-Programmatic Integration Systems, filed on the same date as this application, and U.S. patent application Ser. No. 13/091,632, entitled Safety Methods for Non-Programmatic Integration Systems, filed on the same date as this application, the entire contents of which are incorporated herein by reference.

FEDERALLY SPONSORED RESEARCH OR DEVELOPMENT

Not Applicable.

COMPACT DISK APPENDIX

Not Applicable.

BACKGROUND

1. Field of the Disclosure

The present disclosure relates to electronic content management software and, more particularly, to an integration application.

2. Description of the Related Art

Businesses, educational institutions, and various industries often rely on computing devices and software applications to perform and/or manage their day-to-day operations. In fact, a particular business, educational institution, or industry may rely on multiple software applications to perform and/or manage their day-to-day operations.

Conventional computer networks and processing devices have the capability of multitasking and executing multiple applications simultaneously on a single operating system. For example, it is possible to execute an application for displaying and/or manipulating a document developed by one software provider on a single computer or network of computers while simultaneously executing one or more other applications developed by different software providers for the same purpose on the same single computer or network of computers. Because different applications can process data and documents relating to a common subject or context, it is often desired to seamlessly integrate and use the functionality and features of different applications simultaneously. However, because applications developed by different providers may store, index, and retrieve documents and other data according to their own proprietary formats, such applications may not lend themselves to easy integration.

For a number of reasons, many applications lack the capability for linking, accessing, or otherwise integrating documents and data with other applications. Due to the proprietary nature of software applications, traditional attempts to integrate different applications are often inadequate or unsuccessful. One possible solution involves using programmatic integration that requires modifying the source code of each application. Another possible programmatic solution involves writing specialized source code to integrate one application with another at a code-level through an application programming interface (API) for the other application that is used to push and pull data between the applications. This and other programmatic solutions are generally not desirable due to costs and possible trade secret measures preventing access to the source code. Moreover, it may in fact be contrary to the terms of a license or terms of use for a particular application to attempt to modify or integrate that particular application.

An alternative solution would be to replace the installed applications with a new program suite capable of integration. This solution, however, may be costly and disruptive.

SUMMARY

Integration systems and methods non-programmatically collect application data from a mapped location of a display of an application. The collected application data may be used to notify one or more users that another user is viewing the same collected application data or the same documents.

Disclosed herein are systems and methods of notifying a user of collaboration possibilities when one or more other users view or access the same, similar, or otherwise data.

In one aspect, the collaboration method includes automatically non-programmatically collecting application data from a first mapped location of a mapped source reference of an application used by a first user and automatically non-programmatically collecting application data from a second mapped location of a mapped source reference of an application used by a second user. The integration application determines whether the collected application data from the first mapped location matches the collected application data from the second mapped location, and if the first collected application data matches the second collected application data, that integration application automatically notifies at least one of the first user and second user.

In a second aspect, the collaboration method includes automatically non-programmatically collecting application data from a first mapped location of a mapped source reference of an application used by a first user. The integration application determines whether the collected application data from the first mapped location matches previously collected application data from a second mapped location of a mapped source reference of an application used by a second user; and if the first collected application data matches the previously collected application data, the integration application automatically notifies the first user.

BRIEF DESCRIPTION OF THE DRAWINGS

FIG. 1 is a block diagram of one example embodiment of an application integration system.

FIG. 2 is a block diagram of an embodiment of an application system in accordance with one example embodiment of the application integration system.

FIG. 3 is a block diagram of a database in accordance with one example embodiment of the application integration system.

DETAILED DESCRIPTION

Figure 4:
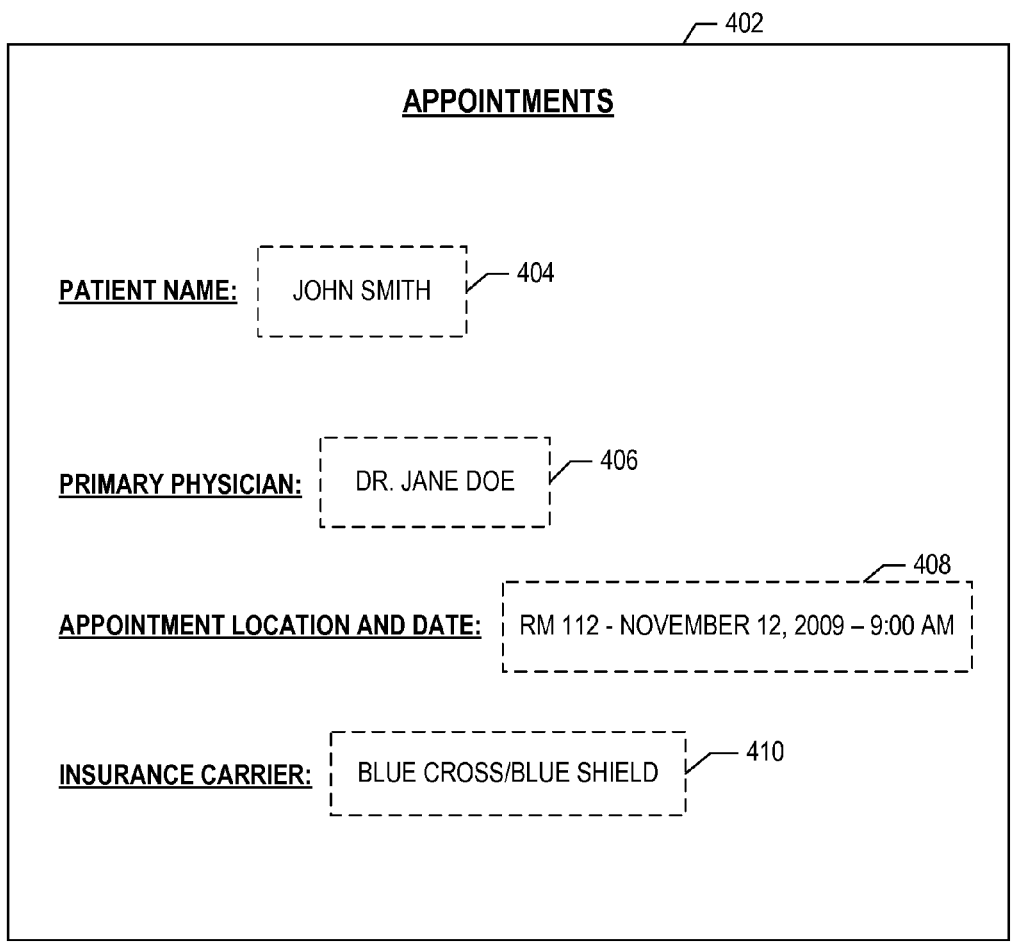
FIG. 4 is a block diagram of an exemplary display containing mapped locations in accordance with one example embodiment of the application integration system.

The following description and drawings illustrate embodiments sufficiently to enable those skilled in the art to practice the present disclosure. It is to be understood that the disclosure is not limited to the details of construction and the arrangement of components set forth in the following description or illustrated in the drawings. The disclosure is capable of other embodiments and of being practiced or of being carried out in various ways. For example, other embodiments may incorporate structural, chronological, electrical, process, and other changes. Examples merely typify possible variations. Individual components and functions are optional unless explicitly required, and the sequence of operations may vary. Portions and features of some embodiments may be included in or substituted for those of others. The scope of the application encompasses the appended claims and all available equivalents. The following description is, therefore, not to be taken in a limited sense, and the scope of the present disclosure is defined by the appended claims.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, the terms "a" and "an" herein do not denote a limitation of quantity, but rather denote the presence of at least one of the referenced item.

Reference will now be made in detail to the example embodiment(s), as illustrated in the accompanying drawings. Whenever possible, the same reference numerals will be used throughout the drawings to refer to the same or like parts.

The systems and methods of the present disclosure provide an application integration system that enables seamless and non-programmatic integration of one or more applications and/or their associated data and/or documents. Moreover, the application integration system enables one or more applications to be integrated without altering or interfering with the operation of the applications. A non-programmatic process is a process that does not rely on the existence of code-level integration or the production of additional source code on a per application basis to gather data to be integrated that is generated from another application. A "per application basis" means that source code is not produced separately for each application that generates data to be integrated. In particular, a non-programmatic process does not modify another application's source code in order to integrate with that application, and the non-programmatic process does not modify its own source code on a per application basis in order to integrate with that application. Accordingly, a non-programmatic system is a system that does not rely on the existence of code-level integration or the production of additional source code on a per application basis to gather data to be integrated that is generated from another application. In particular, a non-programmatic system does not modify another application's source code in order to integrate with that application, and the non-programmatic system does not modify its own source code on a per application basis in order to integrate with that application.

The integration system non-programmatically collects data from one or more mapped locations in one or more applications, such as via an application programming interface (API) for an operating system. In one aspect, the integration system may communicate with one or more applications through a standard or proprietary interface implemented in accordance with protocols of the operating system. In some example embodiments, the interface may be a proprietary interface and/or a combination of a standard and proprietary interface.

An application, as used herein, refers to software or another computer program, other than the integration system or the operating system hosting the integration system, that is executable by a processor and can be stored on computer-readable media. In some example embodiments, an application may refer to firmware and/or a combination of software and firmware. In some other example embodiments, an application may be executed on the web or over a network. An application processes, organizes, manipulates, stores, generates, displays, and/or otherwise renders application data that can be used by the integration system and its associated modules. Application data is the information processed, organized, manipulated, stored, displayed, and/or otherwise rendered by an application.

A mapped location is a spatial or logical location of data or information in an application display or a source reference of the application defined by a user and characterized by the user as being a particular type of data. For example, a mapped location may be defined as a tree node, a Hypertext Markup Language (HTML) tag, an object, coordinates of a display or other user interface screen, a window control or relative to a window control (as described below), or using another data location method. A mapped location can be characterized as any data type capable of being recognized by an application, such as date, a name, social security number, patient identification number, or customer number.

In one aspect, a mapped location is an area of a display containing application data that has been defined and characterized by a user of the integration system. In this aspect, the mapped location may be identified by its spatial location within a display, such as through one or more coordinates. A display, as used herein, refers to a presentation of an image, document, user interface, and/or other application data to a display device. For example, user interface screens for an application, including user interface screens that visually present application data, are displays. One or more displays generated by the application may have one or more mapped locations.

In another aspect, a mapped location is a logical location within a source reference for a display, such as an object or a data element. A source reference, as used herein, refers to a set of instructions, code, and/or application data for a display that is present at a processor and/or memory of the integration system before, during, and/or after it is rendered for display. Thus, the display is the rendered source reference. In one aspect, the source reference exists on the same computing device as the integration system.

The source reference or application data from the source reference may be collected from the API of the operating system by the integration system. For example, the source reference for an HTML page is the HTML code and the application data for the HTML page is collected before, during, and/or after the HTML page is rendered as a display. In this example, the integration system may collect application data from the HTML source reference before, during, and/or after rendering the HTML display. In another example, the source reference for a raster image or a bitmap image may include the code, if any, and the image, including application data within the image, and the image is rendered as a display. In this example, the integration system collects the application data from the source reference image before, during, or after the image is rendered as a display.

In some instances herein, the terms "display" and "source reference" may be used interchangeably. For example, if the integration system collects application data from a display, the integration system effectively collects the application data from the source reference for the display. The source reference, including the application data, is present at the processor and/or memory of the integration system and the integration system collects the application data from the processor and/or memory.

In one aspect, an application display and/or its source reference have one or more application fields, which are locations or areas that contain application data. One or more of the fields may be mapped locations though other fields may not be mapped locations. In one alternate example embodiment, none of the fields are mapped locations. In this aspect, one or more of the application fields may or may not have an associated application label. Application labels are terms used to describe the type, subject matter, nature, and/or may be other designations of the application data in an application field, title bar of an application display, a mapped location, and/or other location of a display or source reference.

FIG. 1 is a block diagram of an embodiment of the application integration system 102. The application integration system 102 monitors applications for application data that can be collected from one or more mapped locations and uses the collected application data to identify documents relevant to the application data, a display, and/or a source reference of the application. The collected application data also or alternately may be used to perform one or more integration functions as discussed more fully below, such as to promote collaboration between one or more users, provide a safety notification or function to a user, and/or synchronize signing a user onto the integration system, among other functions. For example, the application integration system 102 may inspect one or more displays generated by an application or their source references and collect application data from mapped locations of the displays or their source references. The collected application data may be used to identify any documents related to the displays automatically. In another example, the application integration system 102 may inspect a source reference and collect application data from the source reference. The application integration system uses the collected application data for one or more integration functions. The application integration system 102 may include an application system 104, a database 106, and an integration system 108.

The application system 104 may execute one or more applications that are monitored by the integration system 108 and/or from which application data is collected by the integration system. The application system 104 may include one or more modules, applications, and devices to process and generate application data for display.

In one aspect, the application system 104 is a processing system that may include one or more processors, volatile and/or nonvolatile memory, and a data input device, such as a mouse, a trackball, a touch pad, another pointer, a keyboard, another input device or system, and/or combinations of the foregoing. The application system 104 may be embodied in one or more distributed or integrated systems and/or computer-readable media. The application system 104 may also include an image capture device, such as a scanner, to generate electronic reproductions of documents from paper documents. The application system 104 may also include a storage system that stores electronic data, including electronic documents. The application system 104 may also include one or more communication systems that transmit and/or receive user interface screens, application data, electronic documents, and/or other data through wireless and/or wire line communication systems.

The database 106 may include one or more processors and volatile and/or nonvolatile memory and may be a data storage structure or a data storage system executed by the one or more processors on a data storage server. According to one aspect, the database 106 may store documents, files, and/or other data, including projects and tasks, in data fields and/or data tables. A project, as used herein, refers to a collection of documents, files, and/or other data. For example, a project may be the collection of documents that relate to a single identifier, such as a patient or a customer. In another example, a collection may be the collection of documents for a broader subject matter, such as medical testing protocols. A task, as used herein, refers to an item that requires user action. For example, a task may be an approval or confirmation request, a request for user input or response, or a request for digital signature. In this aspect, the database may store application data and documents that may be accessed and/or stored by the integration system 108.

In some other example embodiments, a project may refer to a project within a project. For example, a project may be a collection of documents that relate to each doctor's visit of a particular patient, or a project may be a collection documents that relate to each purchase made by a particular customer.

The integration system 108 monitors one or more applications of the application system 104 and interrogates an operating system to collect application data generated by one or more applications. Interrogating and interrogating an application, as used herein, refer to making a call to the API of an operating system in order to inspect, parse, and/or collect application data from the display and/or the source reference for the application. By way of example, the integration system 108 may locate one or more mapped locations of displays generated by the applications and/or mapped locations of the source references of the applications and collect the application data at those mapped locations. In this example, the integration system 108 monitors and interrogates the applications and/or the operating system for the computing device on or for which the integration system operates and identifies mapped locations for displays (or their source references) when the displays are resident on the computing device on or for which the integration system operates, either on a processor and/or memory of the computing device. The integration system 108 may then collect application data from the mapped locations. The integration system 108 may monitor and/or interrogate data from the application before, during, and/or after the display is rendered.

In one aspect, the integration system 108 may compare the application data collected from the mapped locations with properties of the documents stored in the database 106 to retrieve documents related to the collected application data. In other aspects, the integration system 108 may use the application data collected from the mapped locations for one or more integration functions, including signing a user into the integration system when the user signs into an application from the application system 104 (synchronized sign-on) and/or notifying a user through a user interface when an image or other document or reference displayed or otherwise rendered to the user interface does not correspond to underlying application data or other references, including through audio and/or visual renderings (safety). The integration system 108 also or alternately may use the collected application data for one or more other integration functions, including to display a list of documents or notify the user of a list of documents related to current application data or other references (notification) and/or automatically notify a user when one or more other users view or otherwise render or access application data or references for underlying application data when the other user is simultaneously rendering or accessing or has rendered or accessed application data or references for the same underlying application data (collaboration). In one example, an underlying reference may be a patient or customer identifier, such as a number, and the rendered application data may be data corresponding to the identifier, such as a patient record for the same patient or a customer record for the same customer, respectively.

In one aspect, monitoring and interrogating an application includes collecting one or more displays or source references generated by the application or application data from the displays or source references from the API of the operating system. The integration system 108 makes a call to the API to identify information present in the source references that is relevant to the displays. By way of example and not limitation, the integration system 108 calls the API of the operating system to identify user interface (UI) controls, data at coordinates, the tree structure for a window, children windows, HTML code or its associated data, and/or a bitmap or raster images or portions thereof for a display. As used herein, a UI control refers to an element of a graphical user interface (GUI) that displays or causes the display of an interactive object in a window or a text box. For example, text entry boxes, drop down menus, tabs, labels, any graphical control element, and buttons are UI controls.

In another example, the monitoring of an application and interrogation of the operating system also may occur without rendering the display on a display device. The integration system 108 requests application data for a display from the operating system, and the integration system receives the requested application data from the operating system. In this example, the requested application data need not be displayed. In another example, the application data for the application is effectively rendered in memory and/or on the processor of the integration system 108 and not to a display. For example, a display may be collected by the integration system 108 when the display is rendered in a visible or non-visible user interface of a display device or before or after the display is rendered.

In one aspect, the integration system 108 may be a processing system that includes one or more processors and volatile and/or nonvolatile memory and may be embodied in one or more distributed or integrated components or systems. The integration system 108 may include computer-readable media on which one or more algorithms, modules, software, and/or firmware is loaded and/or operates to implement the methods and systems identified herein, and the algorithms, modules, software, and/or firmware may be executed by the one or more processors. The computer-readable media may include volatile media, nonvolatile media, removable media, non-removable media, and/or other media or mediums that can be accessed by a general purpose or special purpose computing device. For example, computer-readable media may include computer storage media and communication media. Computer storage media further may include volatile, nonvolatile, removable, and/or non-removable media implemented in a method or technology for storage of information, such as computer-readable instructions, data structures, program modules, and/or other data. Communication media may, for example, embody computer-readable instructions, data structures, program modules, algorithms, and/or other data. The communication media may include an information delivery method. The communication media may include wired and wireless connections and technologies and be used to transmit and/or receive wired or wireless communications. Combinations and permutations of the above systems and components described herein may be made.

FIG. 2 is a block diagram of an embodiment of the application system 104A for the application integration system 102. The application system 104A includes one or more custom developed and/or generally commercially available applications, such as the application 202, that are executed by a processor and/or a processing device. The application 202 may include computer instructions, that when executed by a processor, organize, process, manipulate, and/or store data and/or generate one or more displays and/or source references for the displays. The generated displays have application data, and each display may have zero or more mapped locations. The application 202 may also interact with users via one or more user interfaces (not shown). By way of example and not limitation, the application 202 may be a word processing, spreadsheet, image editing, commercial sales, healthcare, and/or academic transcript application. In some embodiments, the application may be an unrelated or host application.

FIG. 3 is a block diagram of an embodiment of the database 106A for the application integration system 102 (see FIG. 1). The database 106A may include one or more documents 302, one or more application plans 304, one or more dictionaries 306, and/or one or more context maps 308. The database 106A may also include a data structure used in place of the dictionary 306, the context maps 308, document 302 and/or the application plan 304, as explained more fully below. Other data may be stored on the database 106A.

By way of example, the document 302 contains information relevant to the application data of the application 202. In other examples, the document 302 may contain other information. In one example, the document 302 may be created using the application 202. In other examples, the document 302 may be created by another application, such as electronic mail, or created from a hardcopy document using an image capture or scanning device (e.g., a scanner or fax machine).

The document 302 may be any file containing text, image and/or other data, such as audio and/or visual data. Some example file formats for documents include, but are not limited to, a text document, portable document format (PDF) document, Tagged Image File Format (TIFF) image, source reference, HTML document, Extensible Markup Language (XML) document, a bitmap image, a .jpeg image, and audio and/or video file.

In one aspect, the document 302 has one or more document properties. A property is a type of data that has a name (i.e., label) and a value. A document property is a type of data associated with a document that describes, identifies, indexes, and/or classifies that document, and the document property has a name (i.e., a label) and a value. In this aspect, the property label identifies the property and the property value is not necessarily populated. A non-populated value is, for example, null, empty, or zero. In one aspect, a value for a property is populated from collected application data. For example, the document 302 may have a property labeled "Zip Code" containing the value "63102." In this example, the property is a five-digit number. The label "Zip Code" describes the nature of the five-digit numerical string and distinguishes the property from other properties that may also be five digit numerical strings, such as an employee identification number, a document number, or telephone extension. The value "63102" may be collected application data from a mapped location. In one aspect, the properties and/or labels may be defined by a user through a user interface.

In another aspect, documents may be indexed using collected application data. Indexing a document means organizing and/or populating or modifying the document properties of the document for storage and/or later identification. For example, the document 302 may indexed by populating the document properties for the document using collected application data. In some example embodiments, indexing a document means organizing and/or populating or modifying the project properties of the project for storage and/or later identification.

The application plan 304 may identify, such as with a list or another representation, one or more displays generated by a particular application that have one or more mapped locations and/or one or more source references used by the application that have one or more mapped locations. For example, the application plan 304 may identify one or more displays generated by the application 202 and/or the source references used to generate the displays that contain one or more mapped locations.

The application plan 304 may temporarily include one or more representations of the displays identified therein. In one aspect, the representations of the displays may be stored temporarily in memory and/or in the application plan 304 and used to identify and/or store one or more mapped locations of the displays. In another aspect, the representations of the displays are not stored in the application plan 304.

In one aspect, the representation of the display may include a listing of the UI controls, a tree diagram, and/or bitmap or raster image representation for the displays identified in the application plan 304. In another aspect, the representation of the display may include another image of each display in the application plan 304. In yet another aspect, the representation of the display may include all of the data selected on user interface, such as through a select or select all and copy function.

The application plan 304 may also include application identifying data and display and/or source reference identifying data. The application identifying data identifies the application as a specific application, such as the application 202, for which the application plan 304 is used. For example, the application identifying data may include the name of the executable file for the application data in the title bar of the displays and/or source references for the application that identify the application, and/or an operating system class identifier that associates the display with the application 202. In some example embodiments, the application identifying data may be a unique application identifier.

In one aspect, the integration system 108 makes a call to the operating system API to determine that the application 202 is being executed on the processor. The integration system 108 then examines the displays and/or source references at the operating system API to identify data in the title bar for the displays and/or source references. The integration system 108 collects the label from the API and processes the application plan 304 to determine if the application plan is applicable to the displays and/or source references.

The display and/or source reference identifying data identifies a display and/or source reference as a particular display and/or source reference within the application plan 304. In one aspect, the display and/or source reference identifying data includes display definitions for each display identified in the application plan 304. For example, the display definitions may include application data and/or other data that is present in the title bar of the particular display. In another example, the display definitions may include one or more mapped locations from which application data can be collected to uniquely identify the display. In yet another example, the display definitions may include one or more mapped locations based upon the active screen or tree controls of an application.

The dictionary 306 is a listing of the data elements that correspond to the mapped locations of one or more displays or source references stored in the application plan 304. In some example embodiments, the dictionary 306 may contain scripts. In one aspect, each data element in the dictionary 306 corresponds to a mapped location of a display or source reference. In another aspect, a data element in the dictionary 306 corresponds to one or more mapped locations. In yet another aspect, a data element in the dictionary 306 corresponds to one or more other data elements in the dictionary. For example, a data element in the dictionary 306 may combine and process one or more other data elements in the dictionary. In this example, a data element named "Full Name" does not correspond to a mapped location, but does correspond to other data elements, such as "First Name" and "Last Name." The data element "Full Name" may process and concatenate the other data elements.

According to one aspect, the application plan 304 has a single corresponding dictionary 306 that characterizes the application data in the mapped locations of the one or more displays of the application 202. According to another aspect, each display in the application plan 304 has its own dictionary. According to yet another aspect, a single dictionary characterizes the application data for more than one application.

Each data element of the dictionary 306 contains the mapped location for the data element in the corresponding display or source reference. In one example, the mapped locations may be defined by name-value pairs within the source references for HTML displays generated by the application 202. In this example, a name is tag or other element in the HTML code, and the value is the application data associated with the name that would be displayed in the HTML-based display. In another example, the mapped location may be defined by coordinates within a display of the application 202 (e.g., Cartesian coordinates based on pixels or other coordinates) or another location designating system. In yet another example, mapped locations may be defined by the UI controls of each display. In still another example, the mapped locations may be defined by the character locations.

In one aspect, the mapped locations of the data elements are logically mapped by the integration system 108. Logically mapping is identifying a logical location or name of a data element (e.g., a node or a tag) rather than a spatial location on the display or source reference. In one example, logical mapping may be achieved by processing a display or source reference and creating a virtual link in memory between each UI control of the display or data elements of the source reference and the application data associated with that UI control or data element. In this example, neither the integration system 108 nor the user needs to identify or determine the spatial location of the application data within the display or source reference. In another example, the integration system 108 identifies each name-value pair from an HTML display or HTML source reference as a data element. The integration system 108 is then able to identify and collect the application data associated with each name-value pair without determining the spatial location of the data in the display. In another example, the integration system 108 uses tags, such as HTML tags and/or tree node addresses, for source references having a tree structure to map locations. Other techniques to map the locations of the application data may be used.

In another aspect, the mapped locations may be spatially mapped by a user. For example, a user may select a spatial position or area on a display, and the integration system 108 assigns pixel coordinates or other coordinates to the selected spatial position or area.

The dictionary 306 may include a label and/or example application data for each data element. The dictionary labels identify the type, subject matter, nature, and/or may be other designations of the application data contained in the mapped location.

In one example, a first mapped location that contains the social security number (SSN) "123-45-6789" would have a dictionary data element that includes the dictionary label "SSN" and example application data "123-45-6789." Similarly, a second mapped location in the same or another display for the same application that contains a patient's first name "Sam" would have a dictionary data element that includes the dictionary label "First Name" and the application data "Sam."

In a healthcare setting having healthcare related applications, another dictionary label may be a patient identification number ("Patient ID"). In the healthcare industry, the Patient ID is a unique sequence of numbers and/or characters used to identify a single patient. In this example, the Patient ID label corresponds to a mapped location of a display generated by a particular application that contains the unique sequence that uniquely identifies each individual patient.

Each application may use a different Patient ID or other unique sequence to identify a patient for which document data, such as a medical file, a medical image, or other data, is currently being displayed. Other mapped locations may be assigned labels, such as Age, Address, Height, and Race. The data in these other mapped locations may be applicable to numerous patients, while the data in locations that correspond to the Patient ID label, however, apply only to a single unique patient. Accordingly, the Patient ID label may be used to associate data from the mapped locations of one or more displays to documents for a particular patient. In addition, the Patient ID label may be useful when using collected application data for one or more integration functions, when the Patient ID format is similar to another commonly used character string such as a social security number, or another unique identifier.

In one aspect, the integration system 108 may create an instance of the dictionary 306 for each application in memory during the execution of the integration system. The instance of the dictionary 306 stores application data collected from one or more mapped locations of a display in memory for one or more dictionary data elements. For example, an instance of a dictionary may contain one or more data elements, and each data element has a mapped location from which application data is collected, the collected application data from the mapped location (if a value exists for the collected application data) A dictionary may also contain a label for the data element. In this example, the spatial or logical location of the mapped location, the collected application data, and the label for the data element are organized and stored in fields corresponding to each data element in the instance of the dictionary 306. In other examples, the instance of the dictionary 306 may have other fields for each data element.

The context map 308 is a data structure containing one or more standardized context map properties that have been mapped from one or more data elements of the dictionary 306 or are otherwise from collected application data. Data elements in the dictionary 306 may use varying terminology for labels. Therefore, the context map 308 maps the data elements and/or otherwise maps collected application data into context map properties that use terminology standardized for the integration system 108.

In one aspect, the context map 308 may define a relationship between the collected application data in an instance of the dictionary 306 and context map properties and/or document properties. In another aspect, the context map 308 may define a relationship with another source of the collected application data. A context map has one or more relationship definitions for one or more context map properties, where each relationship definition identifies a source from which collected application data originates and a destination to which the collected application data from the source is stored for a context map property, at least temporarily. The context map property has a name (i.e., a label) and a value, and the collected application data stored in the destination is the value for the context map property. The context map property labels may be used along with collected application data (which is used as the corresponding context map property value for the property) to query the database 106A for documents or to perform other integration functions. Context map properties may be, for example, a last name, a first name, an address, a postal code, a phone number, a social security number, a student identification, a year, a customer number, a patient name, a birth date, or another name or type of value. In some example embodiments, context map properties may be mapped from data elements in the dictionary 306.

In one aspect, the source may identify collected application data in an instance of the dictionary 306. For example, the source for each context map property is a field of the dictionary that contains the collected application data. In this aspect, the context map properties are standardized properties and can be more easily understood and processed by the integration system 108 than the dictionary labels. For example, a first application may refer to a health care provider as a "physician," a second application refer to the same health care provider as a "doctor," and a third refer to same health care provider as "medic." The dictionaries for these three applications may have three different dictionary labels to describe the same health care provider. The context maps for the displays of the three applications, however, would have the same property label that identifies the health care provider (e.g., "primary physician").

In another example, the dictionary 306 may contain a data element for collected application data "Dean" with the label "Last Name." In this example, however, it may not be clear whether the last name Dean refers to a patient or a health care provider. In this example, the context map property for the display may specify that the data element is a physician last name, thereby refining any queries or integration functions using this data element.

One or more of the data elements identified in the dictionary 306 may be mapped to standardized context map properties that are used by the integration system 108 to use, process, and/or compare the associated collected application data. In addition, one or more context map properties may be associated with one or more documents as a set of document properties that may be used to identify, index, store, query, and/or retrieve the documents, such as the document 302.

In one aspect, each display identified in the application plan 304 may have a unique context map, such as the context map 308. In one example of this aspect, the context map 308 identifies a source and destination for fewer than all of the mapped locations of a display. For example, a display may contain four mapped locations that are identified as data elements in the dictionary 306. However, the context map 308 for the display may identify only two properties that correspond to two of the four mapped locations on the display (one mapped location corresponding to each property) from which the instance of the context map is to be populated. The number of relationship definitions identified in the context map 308, each identifying a source and a destination property, is configurable and may not be equal to the number of mapped locations in the associated display.

In another aspect, one context map may be associated with multiple displays. In one example of this aspect, the context map includes a relationship definition for fewer than all mapped locations of the displays. In some example embodiments, the context map 308 may be omitted.

In one aspect, the context map and the dictionary may be combined into a single data structure. In some example embodiments, the dictionary may not exist, and the source in the relationship definition is the spatial or logical location of the mapped location of a display. For example, a single data structure and/or an instance of that data structure may include the necessary data of the context map 308 and the dictionary 306. In this example, a dictionary and context map may be combined into one data structure that has one or more data elements or properties each identifying a mapped location, collected application data from the mapped location, and a label, such as a standardized label useful for generating queries and/or indexing documents.

In one aspect, the integration system 108 creates an instance of the context map 308 for each display in memory during the execution of the integration system. An instance of the context map 308 includes one or more properties and associated application data collected from the mapped locations of a display. For example, an instance of the context map 308 maps the collected application data from the instance of the dictionary 306 in memory to a value for a context map property that has a label.

FIG. 4 is a block diagram of an exemplary display 402 of application data for an appointment scheduling application. In this example, the appointment scheduling application generates different types of appointment data for a particular patient to a display, such as patient name, physician name, appointment time, and insurance information. For example, a first location 404 on the display 402 includes the patient's name, a second location 406 includes the physician's name, a third location 408 includes the date and time of the appointment, and a fourth location 410 includes the name of the insurance carrier for the patient. The location of the display at which one or more types of appointment data is displayed may be mapped, and the mapped location may be stored in the dictionary 306. Thereafter, the integration system 108 may locate and/or collect the specific appointment data generated by the appointment scheduling application for a particular patient by using the mapped locations of the display.

Figure 5:
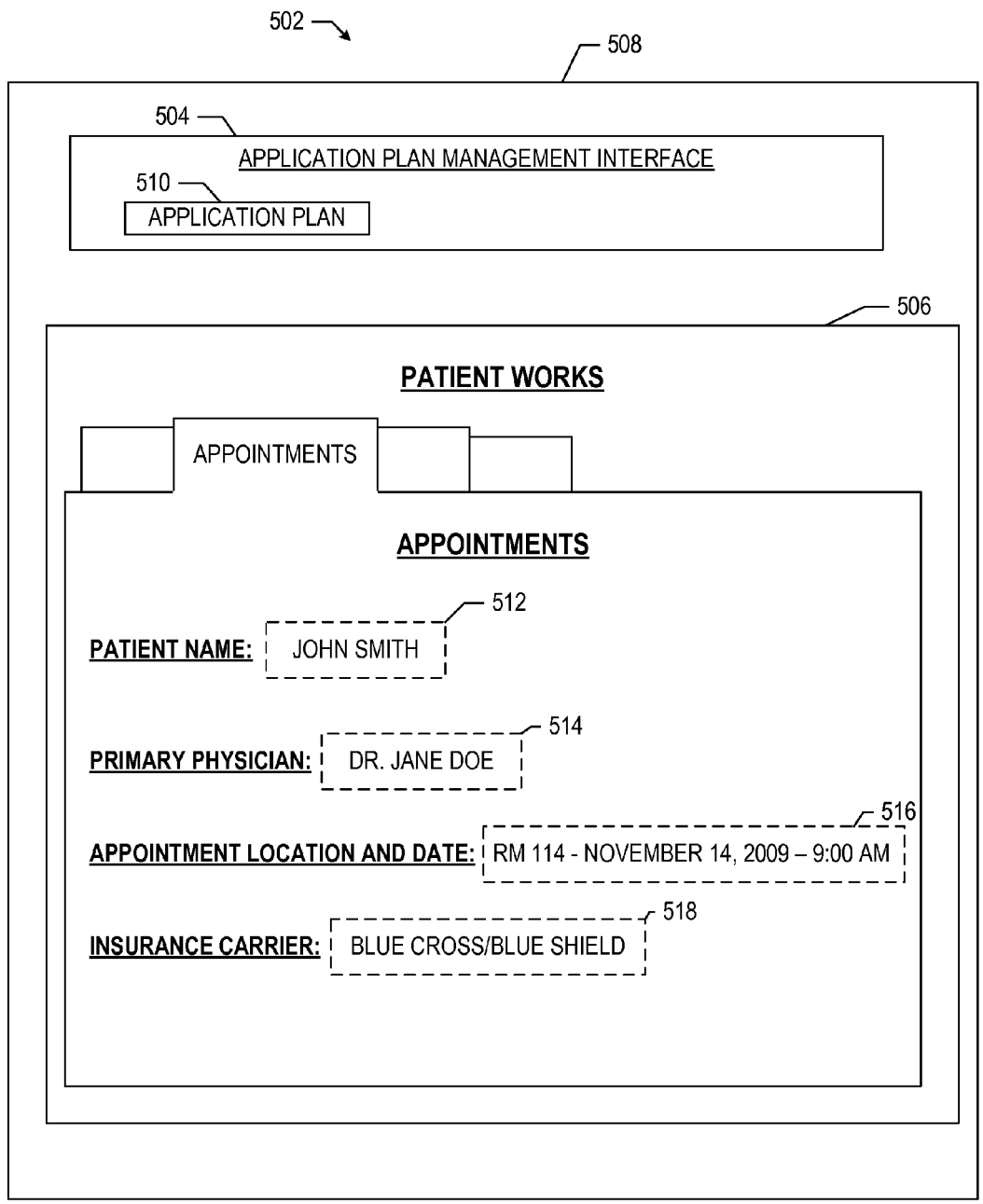
FIG. 5 is block diagram of a application plan management interface for mapping locations of a display in accordance with one example embodiment of the application integration system.

FIG. 5 is a block diagram of a application plan management interface 502 for mapping locations of a display according to one embodiment of the application integration system 102. The application plan management interface 502 may be generated by the integration system 108. According to one aspect, the application plan management interface 502 enables the creation and/or modification of the application plan 304, the dictionary 306, and the context map 308. For example, the application plan management interface 502 may include a toolbar 504 for assigning a display 506 to an application plan using the representation of the display. The application plan management interface 502 may also be used to define the mapped locations and assign labels to the mapped locations for storage in the dictionary 306. In this example, the representation of the display 506 identifies four mapped locations In one aspect, the representation of the display 506 may be a tree structure depicting the UI controls and/or other data elements of the display. In another aspect, the representation of the display 506 may be a bitmap for the display, as shown in FIG. 5. In this aspect, the application plan management interface 502 has one or more menus and/or buttons, such as an application plan button 510. As used herein, a button refers to a simulated selection interface generated for display that is selected by a user input. The selection of a button activates a specific function within the application plan management interface 502.

The application plan button 510 may be selected to create or modify the application plan 304. For example, one or more application displays may be added to the application plan 304 if it is determined that the one or more application displays contain application data of interest.

In one aspect, once a display has been selected for inclusion in the application plan 304, the integration system 108 automatically logically identifies and maps the locations of the data elements and/or UI controls for the display 506 and presents a list or tree structure of the logically mapped data elements found in the display to the user as the representation of the display. From the representation of the display 506, the user may select one or more data elements to be added to the dictionary 306. For example, the user may move data elements from the representation of the display to the dictionary 306 using one or more methods. Because the spatial or logical location of the data element is known from the representation of the display, the integration system 108 may store the spatial or logical mapped location of the data element in the dictionary 306. For example, a user may select and drag the data element "Jones" to the dictionary 306 from a logically mapped tree structure representation of the display. In this example, the integration system 108 may also store the logical location for the "Jones" UI control in the dictionary as the mapped location of the data element.

In another aspect, the integration system 108 enables the user to spatially define one or more mapped locations, such as in a bitmap or raster representation of the display 506. For example, a user may select a data element in a bitmap representation of the display 506, and the integration system 108 automatically identifies and stores the location of the data element by defining boundaries around the selected data element. In some alternate example embodiments, the user may draw a box or other boundaries around the selected data element. In another example embodiment, the integration system 108 may identify a selected location on the representation as a UI control and store the location of the UI control and/or an application field or data associated with the UI control as a mapped location in the dictionary 306. In still other example embodiments, a mapped location may be determined by the screen or display coordinates or a character offset.

As the UI control names may be unique to each application and display 506, the user may, in one aspect, select a label to be associated with the data element. For example, the user may input a label as text using a text entry box (not shown). In another example, the label assigned to the mapped location of the display 506 in the dictionary 306 may be the same as the label used by the application. In another example, the integration system 108 may automatically select the application label from the display 506 and store it as the dictionary label.

According to another aspect, the integration system 108 may automatically identify and map locations of the display 506 based upon the nature of the display. For example, the integration system 108 may automatically identify the display 506 as an HTML display, capture the HTML source code for the display, parse the source code, identify name-value pairs within the source code, and store the name-value pairs as logically mapped locations in the dictionary 306. In another example, the integration system 108 may automatically determine that the display 506 has a source reference structured as a hierarchical tree with one or more linked nodes. In this example, the integration system 108 may automatically identify the nodes and store the nodes as logically mapped locations in the dictionary 306. In other example embodiments, the integration system may automatically identify and map locations of the display 506 based upon a bitmap.

In one aspect, the integration system 108 may create and store the application plan 304, the dictionary 306, and the context map 308 as files in the database 106A. In another aspect, the data from the application plan 304, the dictionary 306, and the context map 308 may be stored in fields and/or tables in the database 106A. In yet other aspects, the data from the application plan 304, the dictionary 306, and the context map 308 may be stored in other ways.

In yet another aspect, the application plan management interface 502 may be generated for display by a stand-alone application (not shown) that is not part of the integration system 108 to create and/or modify the application plan 304, the dictionary 306, the context map 308, and/or another data structure used in place of the dictionary and context map. In this aspect, the stand-alone application may then be used to define mapped locations of the display 506.

Figure 6:
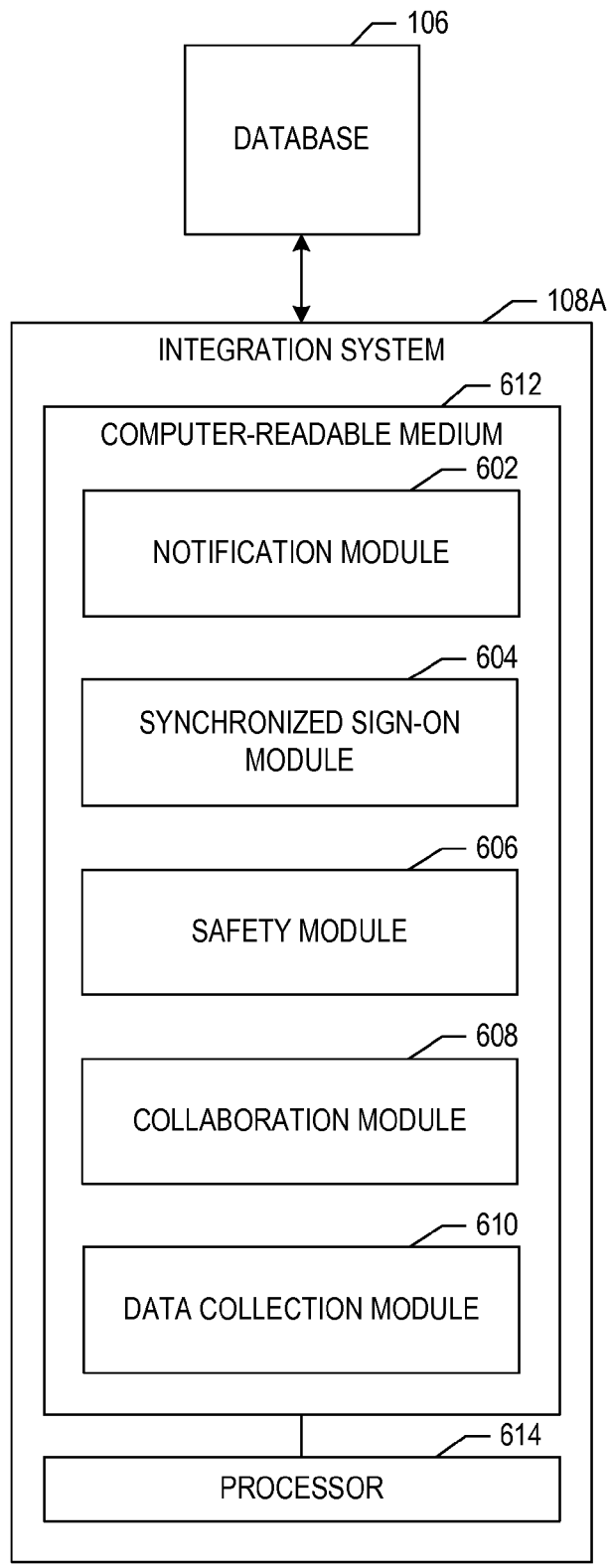
FIG. 6 is a block diagram of an embodiment of an integration system in accordance with one example embodiment of the application integration system.

FIG. 6 is a block diagram of an embodiment of the integration system 108A for the application integration system 102. The integration system 108A may include a plurality of modules 602-610 that are stored on a computer-readable medium 612 and are executed by a processor 614. The modules may include a notification module 602, a synchronized sign-on module 604, a safety module 606, a collaboration module 608, and a data collection module 610, all of which non-programmatically collect data from one or more applications. The modules 602-610 and/or their functionality may be integrated or distributed in the application integration system 102. In some example embodiments, some of the modules 602-610 may be omitted or additional modules may be included in the integration system 102.

In one aspect, the modules 602-610 non-programmatically collect application data from the application 202. In this aspect, the integration system 108A requests data from the operating system API. The integration system 108A calls the operating system API to request a standard interface generated by the application 202. The operating system API presents the standard interface for the application 202 to the integration system 108, which collects application data from the interface using standardized operating system protocol communications. The modules 602-610 may collect application data from source references and/or displays that are not rendered for display on a display device. In another aspect, the modules 602-610 non-programmatically collect the application data from rendered displays.

In one aspect, when two or more modules are integrated, one or another, but not both or all, collect application data from the mapped locations using an instance of a dictionary 306 and one or more context maps 308. In some alternate example embodiments, those processes may be performed in a separate data collection module. The remaining processes of each module may be performed by the respective module.

The notification module 602 may collect application data from a display or a source reference for a display generated by the application 202. The notification module 602 automatically queries the database 106A to identify documents, such as the document 302, that are relevant to the application display or application data of the display. The notification module 602 may also query the database 106A to identify other projects, tasks, and/or other stored data.

In one aspect, the notification module 602 may collect data from one or more mapped locations of the source reference or the display generated by the application 202. The notification module 602 may use the collected application data to query the database 106A to identify one or more documents that are associated with the collected application data. For example, the notification module 602 may collect the application data "John Smith." The notification module 602 may use "John Smith," alone or in combination with other collected application data, to identify all documents related to "John Smith" or a subset thereof.

In another aspect, the notification module 602 may use context map properties and their associated labels and values to query documents. For example, the notification module may build a query to search for documents having a document property name (i.e. a label) and an associated document property value equal to a context map property label and its associated context map property value, where the context map property value is the value of the collected application data.

The synchronized sign-on module 604 automatically signs a user of the application 202 on to the integration system 108A. For example, the sign-on module may non-programmatically collect application data identifying the current user of the application 202 from a mapped location of the application and automatically sign the current user on to the integration system 108A as the current user of the integration system. Similarly, the sign-on module 604 may sign a user out of the integration system 108A in response to changes in or the lack of application data in the mapped location of the application 202.

The safety module 606 protects against the inadvertent display of a document, such as the document 302, if the document is not associated with the application data currently being viewed by the user. The safety module 606 compares the current collected application data to the data associated with the document to determine if the document is associated with the current application data. In one aspect, the safety module 606 may close the display of the document 302. In another aspect, the safety module may notify a user through a user interface if the application data currently being viewed does not correspond to the data associated with the document.

In one example, the safety module 606 may collect the application data "Jane Doe" from a mapped location of a new display of the application 202, while a document containing the lab results for John Doe is also displayed. The safety module 606 compares a context map property having the collected application data "Jane Doe" as a value with a context map property used to retrieve the document (e.g. "John Doe") to determine that the display and the document do not refer to the same patient. In this example, the safety module 606 may automatically close or prompt the user to close the document. In some example embodiments, the safety module 606 may generate an icon or other graphic or message for display to notify the user. In some other example embodiments, the safety module 606 may generate or play an audio signal to notify the user. In yet other alternate embodiments, the safety module 606 may compare the application data "Jane Doe" with collected application data used to retrieve the document, without reference to the context map 308, to determine that the display and the document do not refer to the same patient.

In another example, the safety module 606 may collect application data from a mapped location of the display and compare the context map properties for the display to the document properties. If the context map properties do not match the document properties, the safety module 606 may automatically close or prompt the user to close the document. In some other example embodiments, the safety module 6-6 may generate an icon or other graphic message for display to notify the user. In some other example embodiments, the safety module 606 may generate or play an audio signal to notify the user.

In another example, the safety module 606 may collect application data from one or more mapped locations of a display and compare the collected application data to one or more document properties of an open document. If the collected application data does not match the document properties, the safety module 606 may automatically close or prompt the user to close the document. In some other example embodiments, the safety module 606 may generate an icon or other graphic message for display to notify the user.

The collaboration module 608 may notify one or more users of the application integration system 102 if another user has viewed or is currently viewing the same, similar, or related application data and/or documents. For example, when one user (e.g., doctor) is viewing an application displaying the patient chart for a Patient A, and another user (e.g., a pathologist) is viewing an application displaying laboratory results for Patient A, the collaboration module 608 detects that both users are viewing application data associated with Patient A and notifies one or both users that at least one other user is viewing data for Patient A.

In one aspect, the collaboration module 608 enables a user to configure a notification time period. The notification time period is a time period (e.g. minutes, hours, days, or months) from which a first user will be notified if another user views, accesses, or modifies application data that is the same, similar, or related to the application data being viewed by the first user. The actions of the other user may occur prior to or subsequent to the viewing by the first user. In this aspect, any user may leave comments, notes, or other information for other users who view the same, similar, or related application data.

The data collection module 610 monitors the application 202 continuously or at a predetermined interval such as specific day of the week, time or time interval and locates one or more mapped locations in one or more displays for the application by processing the spatial or logical locations of the mapped locations stored in the dictionary 306 for the application. The data collection module 610 may also collect application data from the mapped locations and populate instances of the dictionary 306 and the context map 308. In one aspect, the data collection module 610 may use collected application data to index documents, other objects, projects, and/or tasks stored in the database 106A.

In some example embodiments, one or more modules 602-610 may identify mapped locations in one or more displays for the application 202 by processing the spatial or logical locations for the mapped locations stored in the dictionary 306 for the application, collecting application data from the mapped locations, and populating instances of the dictionary and the context map 308.

Figure 7:
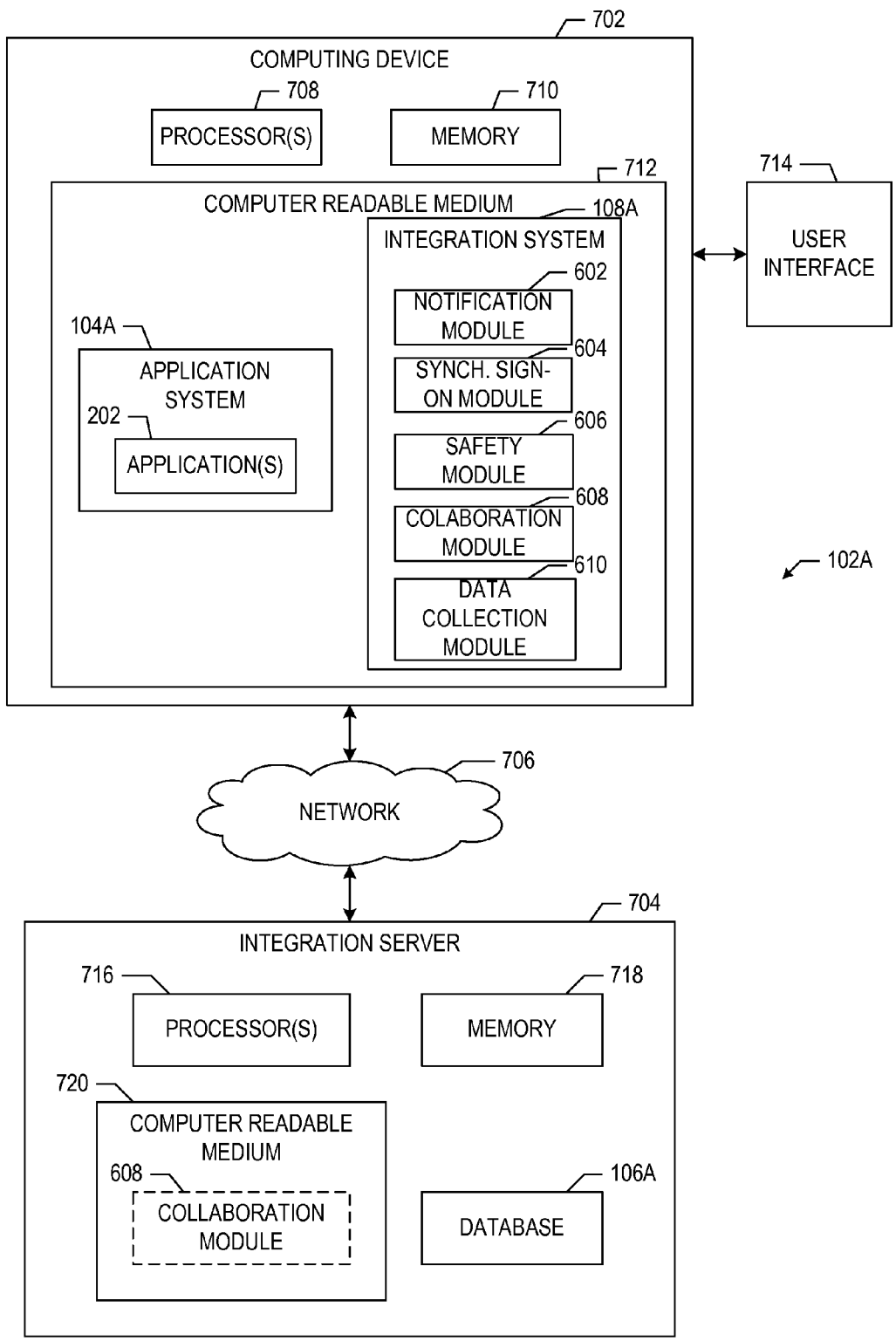
FIG. 7 is a block diagram of one example embodiment of the application integration system.

FIG. 7 is a block diagram of one example embodiment of the application integration system 102A. The application integration system 102A includes a computing device 702 and an integration server 704 that may communicate through a network 706 or a direct connection. In this example embodiment, the functionality of the integration system 108A and the application system 104A are realized on the computing device 702. For example, the application system 104A may reside on the computing device 702, as shown in FIG. 7, or as a separate system or server that communicates with the computing device, such as through the network 706 or a direct connection.

The computing device 702 is a processing device, such as a personal computer, server computer, or mobile processing device. It will be appreciated by those skilled in the art that other processing devices may also be used. The computing device 702 may have one or more processors 708 that process software or other machine-readable instructions and memory 710 to store the software or other machine-readable instructions and data. The memory 710 may include volatile and/or non-volatile memory. The computing device 702 may communicate with the integration server 704 using wired and/or wireless communication through a direct connection or via the network 706.

The computing device 702 may execute one or more modules, such as one or more of the modules 602-610 of the integration system 108A, that are stored on a computer-readable medium 712. The computing device 702 may also execute one or more applications, such as the application 202 of the application system 104A, that are embodied on machine-readable media, such as the computer-readable medium 712 or another computer readable medium. The computing device 702 may also receive and transmit communications from and to an external application system executing the applications. The computer-readable medium 712 may include volatile media, nonvolatile media, removable media, non-removable media, and/or other media or mediums that can be accessed by a general purpose or special purpose computing device. For example, the computer-readable medium may include computer storage media and communication media. Computer storage media further may include volatile, nonvolatile, removable, and/or non-removable media implemented in a method or technology for the storage of information, such as computer-readable instructions, data structures, program modules, and/or other data. Communication media may, for example, embody computer-readable instructions, data structures, program modules, algorithms, and/or other data. The communication media may also include an information delivery method. The communication media may include wired and/or wireless connections and technologies and be used to transmit and/or receive wired and/or wireless communications. Combinations and permutations of the above systems and components described herein may be made.

The computing device 702 may also include an input system (not shown) and a display system (not shown). The display system, for example, may have a monitor or other device for rendering displays, including application data and other data. Such display systems may include, for example, touch screen displays or graphical user interfaces.

The input system may include one or more systems, devices, or components used to generate or transmit an electronic version of one or more documents and other data for the application integration system 102A. The input system may include a scanner that scans paper documents to create electronic reproductions of the documents that are to be used by the integration system 108 and/or the application system 104. The input system may also include one or more processing systems and/or communication systems that transmit and/or receive electronic documents and/or other data through wireless or wire line communication systems to the computing device 702, such as a scanner, image capture device, facsimile machine or electronic mail component. The input system may further include one or more processors, a computer, volatile and/or nonvolatile memory, a mouse, a trackball, a touch pad, a keyboard, and/or a combination of the foregoing. The input system may be embodied by one or more processors or processing systems, one or more distributed or integrated systems, and/or computer-readable media.

In one aspect, the application integration system 102A may include a user interface 714 for providing data and/or instructions to the integration system 108A and for receiving data and/or instructions from the integration system. The user interface 714 may display data from the integration system 108A, including one or more displays, and enable a user to enter data and/or instructions. The user interface 714 may be embodied in or operate using one or more processors or processing systems, such as with the display system. The user interface 714 may also be embodied in or operate using one or more distributed or integrated systems and/or computer-readable media. In some example embodiments, the user interface 714 may have an audio component for generating or playing audio signals.

The integration server 704 has one or more processors 716 and memory 718 to store and execute software or other machine-readable instructions and data. The memory 718 may include volatile and/or nonvolatile memory. The integration server 704 may also include the database 106A. In another aspect, the collaboration module 608 may be embodied on the computer-readable storage medium 720 that resides on the integration server 704 instead of in the integration system 108A. In another example embodiment, the collaboration module may be embodied on a computer readable storage medium that resides in application system 104A.

The network 706 is the Internet, an intranet, an Ethernet network, a wire line network, a wireless network, another communication network, and/or combinations of the foregoing.

Figure 8:
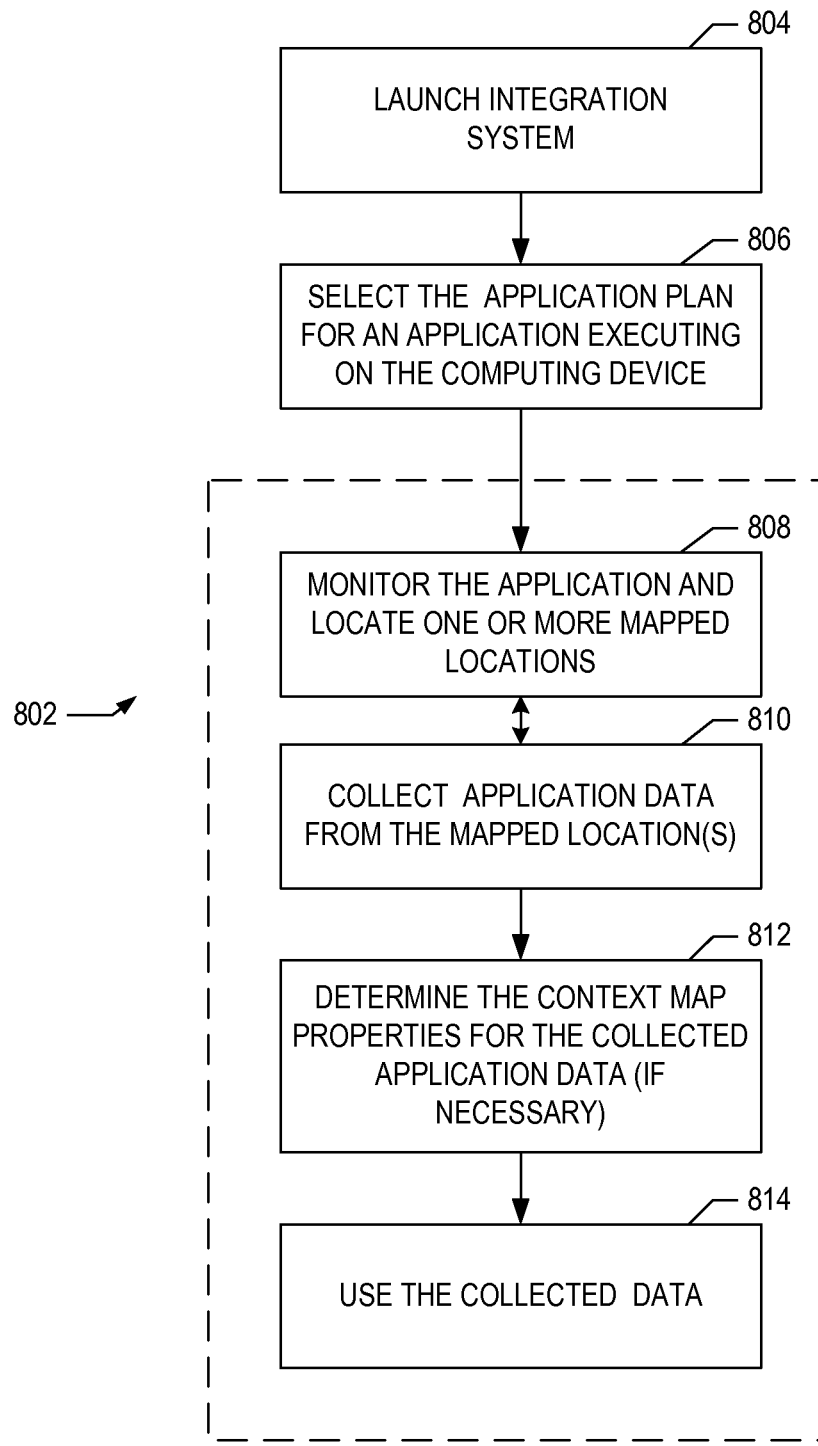
FIG. 8 is a flow diagram of an application data collection process in accordance with one example embodiment of the application integration system.

FIG. 8 is a flow diagram depicting an example of an application data collection process 802, as carried out by an embodiment of a data collection module 610 of the application integration system 108A (see FIG. 7). After the integration system 108A is launched at block 804, the application plan is selected at block 806. In one aspect, the user may select the application plan for the application 202 that is executing on the computing device 702. In another aspect, a configuration file is processed by the processor of the computing device may select the application plan to use for the application 202. Therefore, the user need not select the application plan when the application data collection process 802 is carried out. In yet another aspect, the application plan to be used may be selected based upon the executable files for one or more applications currently executing on the computing device.

At block 808, the data collection module 610 of the integration system 108A continuously monitors the application 202 to identify each display that is generated for viewing on a display device. The data collection module 610 may identify one or more mapped locations in a display and collect application data from the mapped locations at block 810. In one aspect, the collected application data may be used to populate an instance of the dictionary 306.

In one aspect, the display is an image, and the application data may be collected from a mapped location of the image. The application data at the mapped location may be collected as an image. An image-based format is a graphical representation of collected application data that may include characters as part of the image. In this aspect, the integration system 108A may conduct a character recognition, a character voting, and/or an image registration process to identify the collected application data as text.

According to another aspect, the data collection module 610 of the integration system 108A may inspect the source references of the displays to locate the application data that appears in the mapped locations. For example, name-value pairs may be located in an HTML source reference. Once the name-value pairs have been located, the data collection module 610 may collect the application data identified by the name-value pair from the source reference. In another example, the data collection module 610 of the integration system 108A may inspect source references to identify tags, such as HTML tags and/or tree node addresses for source references having a tree structure, and collect the data corresponding to the tags and/or tree node addresses.

In yet another aspect, the data collection module 610 of the integration system 108A may refer to the logical associations created during the logical mapping of the display. In this aspect, the data collection module 610 of the integration system 108A may collect the application data associated with the UI controls found in the display or source reference.

At block 812, the integration system 108A may refer to the context map 308 for the dictionary 306 to determine the context map properties for the collected application data. At block 814, the data collection module 610 of the integration system 108A may use the context map properties (including the context map property values and/or the associated context map property labels) to query the database 104A or perform another function using the notification module 602, sign the user of the application 202 on to the integration system 108 using the synchronized sign-on module 604, and/or determine if the properties of any documents currently being displayed are not associated with the collected application data and/or context map properties using the safety module 606. The collected application data and/or context map properties may also be used to promote collaboration between one or more users of the application integration system 102 using the collaboration module 608. When the data collection module 610 is used with the modules 602-608, the modules need not perform the data collection processes performed by the data collection module 610. In such example embodiments, the modules 602-608 perform their remaining processes.

In one aspect, the modules 602-608 may use only the collected application data for the query or other functions without reference to the corresponding context map properties. In this aspect, the context maps are not used, and the collected application data for the query or other function may be taken from the dictionary and/or other data structure and not the context map property values.

According to another aspect, the application data collection process may execute automatically and/or continuously upon the execution of the application 202. In this aspect, the application data collection process of the data collection module 610 occurs without requiring user initiation or continued user input. In one aspect, one or more modules 602-608 also automatically and/or continuously perform their functions without requiring user initiation or continued user input. As used herein, automatically means without user initiation.

Figure 9A:
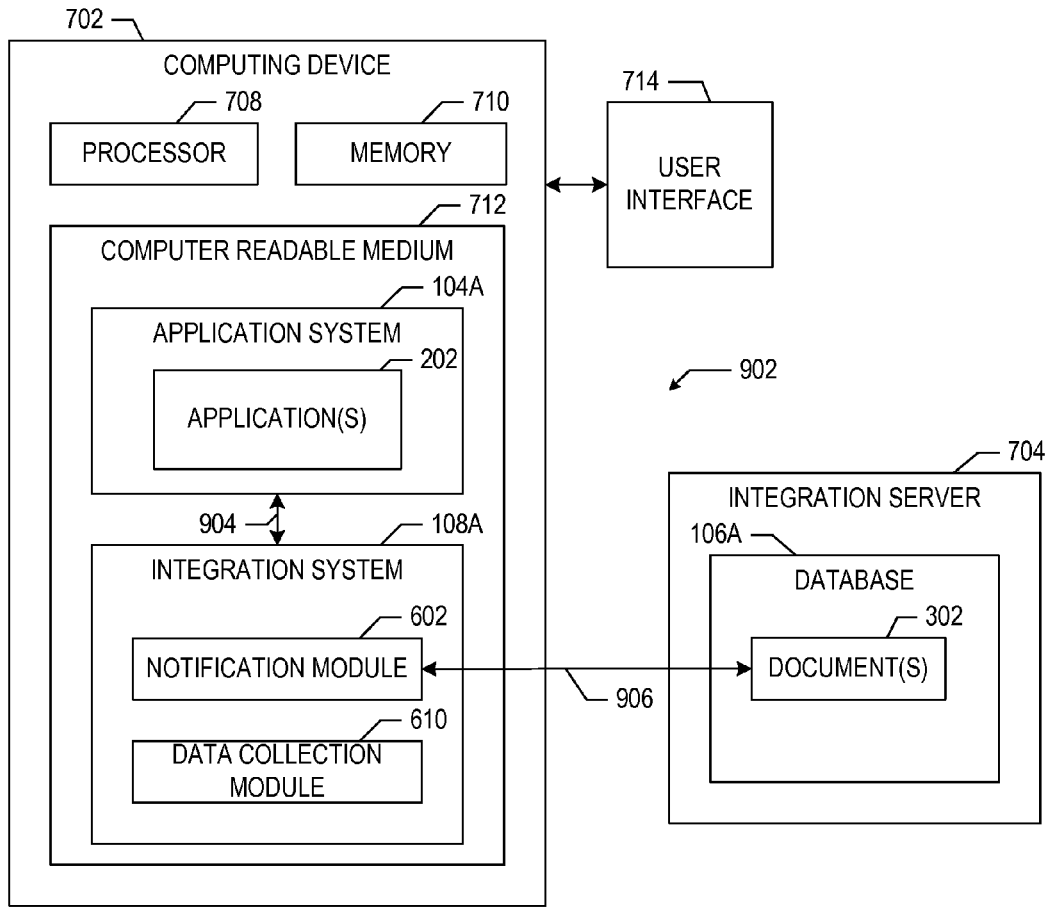
FIG. 9A is a block diagram of a notification function in accordance with one example embodiment of the application integration system.

FIG. 9A is a block diagram depicting an example of the notification functionality 902 as realized by the notification module 602 of the integration system 108A. For purposes of illustration, only the notification module 602 has been shown within the integration system 108A, and only the database 106A and the document 302 are shown within the integration server 704. While the application system 104A is shown to be part of the computing device 702 in FIG. 9A, the application system 104A may be external to the computing device.

According to one aspect, the computing device 702 or an external application system may execute the application 202 that generates one or more displays (not shown). When at least one display is generated, the notification module 602 may non-programmatically collect application data from one or more mapped locations of the display at the operating system API, as indicated by block 904. The notification module 602 may process the instance of the context map 308 containing the context map properties with the context map property labels and/or the associated collected application data as the context map property values to generate a query 906 of the database 106A. The query 906 may use the context map properties to identify documents having properties that satisfy the query. For example, if the instance of the context map 308 has a context map property labeled "Patient Last Name" and the collected application data associated with that property is "Smith," the notification module 602 queries the database 106A to identify one or more documents having a document property labeled "Patient Last Name" and an associated value of "Smith." Therefore, the notification module 606 will identify one or more documents corresponding to the instance of the context map 308 and thus relevant to the display.

If a document, such as the document 302, is identified by the query 906, the document 302 may be retrieved by the notification module 602, and the document or a link to the document may be generated to the user interface 714. If more than one document is identified, the notification module 602 may generate a list containing links to the documents. Such list of documents may then be displayed on the user interface 714. In some example embodiments, thumbnails or image previews of the documents may be generated and displayed.

In one aspect, the notification module 602 may be automatically and continuously executed to detect any changes in the display generated by the application 202. To detect changes, the notification module 602 non-programmatically polls the display, polls the source reference for the display, and/or otherwise collects data from the operating system API to identify and collect application data from any mapped locations in the display. The notification module 602 may generate a new query, similar to the query 906, to query the database 106A to identify documents that have properties associated with the context map properties (including values of the newly collected application data and/or labels). In some example embodiments, notification module 602 may generate a query with the newly collected application data without reference to the context map properties. Thus, any newly identified documents may be proactively provided to the user in response to changes in the application display without requiring continued user input.

In another aspect, the user may be notified that the document 302 has been identified, without displaying the document. For example, a notification, such as a pop-up message or graphic icon may be presented to the user. When the user uses the input device to hover over the notification, the document 302 may be displayed as a thumbnail or in a separate window. In some example embodiments, when the user uses the input device to select or activate the notification, the document 302 may be rendered for display on the display device.

Figure 9B:
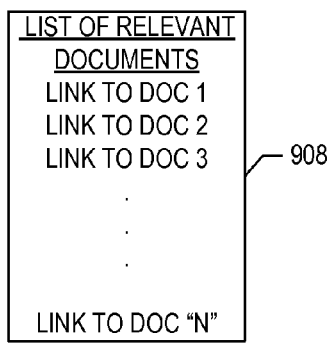
FIG. 9B is block diagram of an example document list retrieved in response to the notification function in accordance with one example embodiment of the application integration system.

FIG. 9B depicts an example document list 908 that may be generated by the notification module 602 and viewed on the user interface 714. In this example, the document list 908 may include documents having one or more properties in common with the context map properties in common with the collected application data, without reference to the context map properties. As shown in this example, the document list 908 may include links that may be selected by the user from the user interface 714 to retrieve one or more documents.

Figure 10:
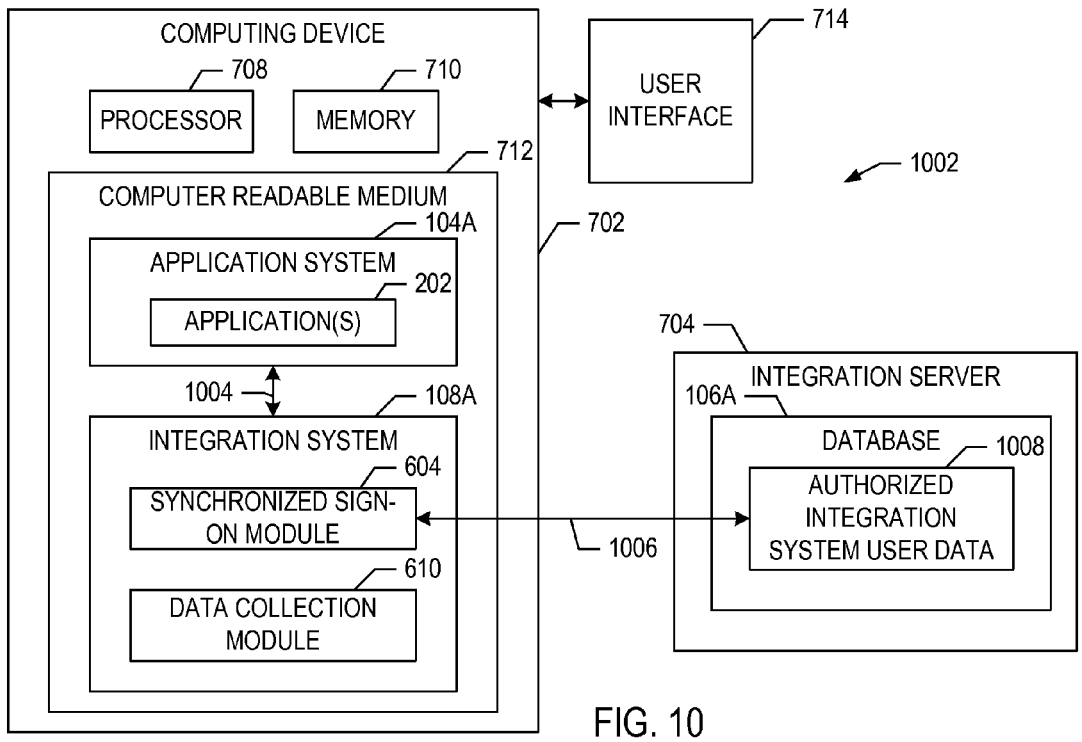
FIG. 10 is a block diagram of an automatic sign-on/sign-off function in accordance with one example embodiment of the application integration system.

FIG. 10 is a block diagram depicting an example of the automatic sign-on and sign-off functionality 1002 as realized by the synchronized sign-on module 604 of the integration system 108A. For purposes of illustration, only the sign-on module 604 has been shown within the integration system 108A, and only the database 106A and the authorized integration system user data 1008 are shown within the integration server 704. The authorized integration system user data 1008 contains the unique identifiers for all users that are authorized to sign on to the integration system 108A. Such identifiers for authorized users of the integration system 108A may be but are not limited to user names, numbers. While the application system 104A is shown to be part of the computing device 702 in FIG. 10, the application system may be external to the computing device.

In one aspect, only users that are signed on to the integration system 108A may use the features and functions performed by the integration system 108A modules, such as the notification module 602, the safety module 606, and the collaboration module 608 or any combination of the foregoing. The computing device 702 may execute the application 202 that generates one or more displays (not shown). When at least one display is generated, the synchronized sign-on module 604 may non-programmatically collect application data identifying the current user of the application 202 from a mapped location of the display, as indicated by 1004. For example, a display may include the application user name for the user of the application 202 in the title bar or a mapped location of an application window. In this example, the synchronized sign-on module 604 non-programmatically collects the application user name from the title bar of the window, from the source reference for the window, and/or from data otherwise collected from the operating system API. The synchronized sign-on module 604 may determine if the application user name corresponds to a user name that is authorized to sign on to the integration system 108A.

If, for example, the application user name is the same as the integration system 108A user name, then the synchronized sign-on module 604 may automatically sign the user into the integration system without requiring additional user input. In another example, the application user name may be different than the integration system 108A user name for the same user. In this example, the sign-on module 604 may refer to the authorized integration system user data 1008 to determine if the application user name corresponds to an authorized user name, as indicated by 1006. If an authorized user name is identified, the synchronized sign-on module 604 may sign the user on to the integration system 108A using the authorized user name. If the application user name does not correspond to an authorized user of the integration system 108A, the user is not signed on to the integration system. Furthermore, if no application user name is collected or the application user name does not correspond to an authorized user name, the sign-on module 604 does not sign the application user on to the integration system 108A. In other example embodiments, other unique user authentication credentials, such as a user identification number, may be used to sign in on to the integration system 108A.

In another aspect, the integration system 108A may presume that a user who successfully signs on to the application 202 is automatically authorized to use the integration system. In this aspect, the synchronized sign-on module 604 may poll the display, poll the source reference for the display, and/or otherwise collect data from the operating system API to identify and collect application data from the mapped location that indicates that the user is signed on to the application 202. The synchronized sign-on module 604 may automatically sign the user on to the integration system 108A without referring to the authorized integration system user data 1008. For example, no password or other user credentials from the application 202 are required to sign the user on to the integration system 108A.

The synchronized sign-on module 604 may execute automatically and continuously. The synchronized sign-on module may continuously compare the application user identifier, such as a number or name, if any, against the authorized integration system user data 1008. If no application user identifier is collected or the application user identifier no longer corresponds to an authorized user of the integration system 108A, the synchronized sign-on module may automatically sign the current user of the integration system 108A off of the integration system.

Figure 11:
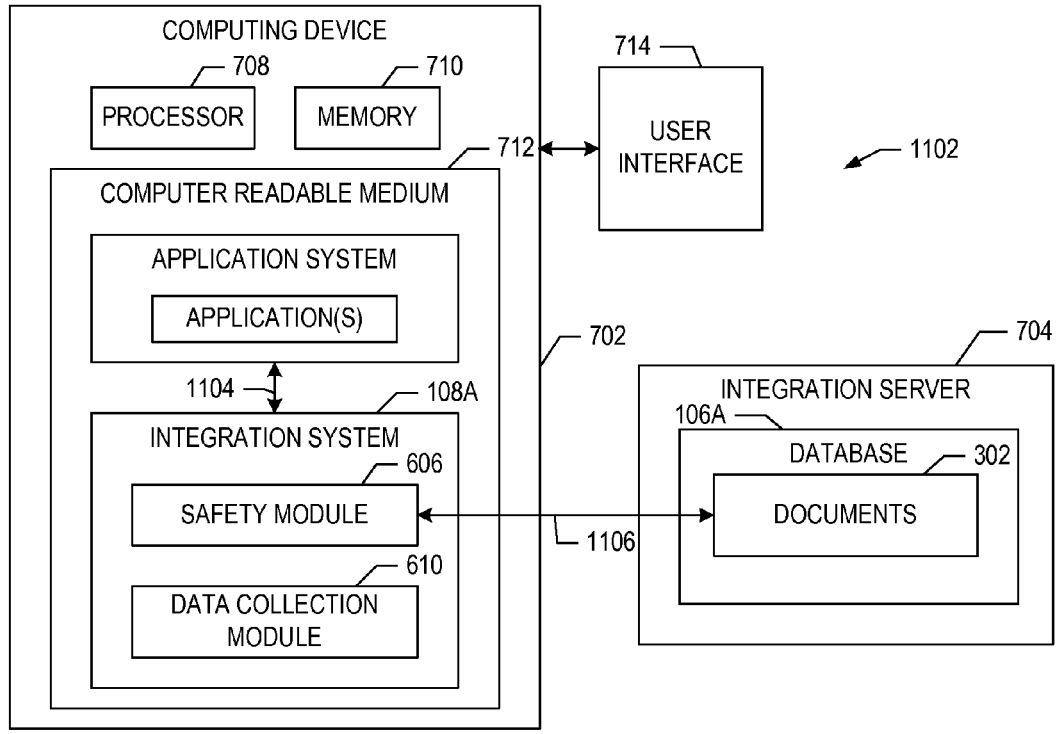
FIG. 11 is a block diagram of a context safety function in accordance with one example embodiment of the application integration system.

FIG. 11 is a block diagram depicting a context safety functionality 1102 as realized by the safety module 606 of the integration system 108A. For purposes of illustration, only the safety module 606 has been shown within the integration system 108A, and only the database 106A and the document 302 are shown within the integration server 704. While the application system 104A is shown to be part of the computing device 702 in FIG. 11, the application system may be external to the computing device.

The unintentional display of a patient or financial data document for one patient or customer along side application data for another patient or customer may lead to a misdiagnosis or misinformation and may result in a violation privacy laws, a security breach and/or other issues. A patient data document is a document containing data regarding a patient. For example, a patient data document may be a medical record, patient test results, a biographical data form, or other patient records. A financial data document is a document containing financial information and may be, for example, a bank statement, loan application, etc. By way of example and not limitation, the patient or financial data document may be an image, an HTML page, a PDF file, and/or another display type. The safety module 606 non-programmatically minimizes the risks of the unintentional reliance on the incorrect patient or financial data document.

The safety module 606 may non-programmatically identify and collect application data from the mapped locations of one or more displays, as indicated by 1104. The safety module 606 may collect the application data from the displays, the source references for those displays, and/or data may otherwise be collected from the operating system API. The safety module 606 compares the collected application data to data associated with the document to determine if a discrepancy exists. In one aspect, the safety module 606 may compare collected application data (without reference to the context map 308) to document property values for any document that is currently displayed. If the collected application data does not match the document property values, the safety module 606 may automatically close the document. In some other example embodiments, the safety module 606 may notify the user in lieu of or in addition to closing the document.

In one aspect, the computing device 702 or an external application system may execute an application 202 that generates one or more displays (not shown) while a patient data document is also displayed. In one aspect, the patient data document may be identified and retrieved by the notification module 602 as described above. In this aspect, a first instance of the context map 308 used to identify the patient data document retained in memory. For example, the patient data document may be retrieved by the notification module 602 following a query using the first instance of the context map 308 for a first display that is no longer rendered for viewing. The notification module 602 may query the database 106A to identify and retrieve the patient data document that has one or more document properties equal to the context map properties for the first display.

In another aspect, the application data collected by the safety module 606 or the data collection module 610 may be used to populate a second instance of the context map 308 for the displays. The safety module 606 may determine if a discrepancy exists between the first instance of the context map 308 and the second instance of the context map. In one example, the second instance of the context map 308 may be created when the display changes or when application data for the display changes. In this example, the safety module 606 may automatically close all open documents and/or notify a user when the context map property values for the first instance of the context map 308 change or when the properties of a second instance of a context map do not match the properties of the first context map instance.

In one aspect, if any discrepancy is identified between the first and second instances of the context map 308, the safety module 606 automatically closes the display of the document.

This may be done to prevent the user from inadvertently relying on the data in the document when evaluating the application data appearing in one or more displays.

In another aspect, a collection of documents (e.g., a folder of documents) may be retrieved and displayed in response to a query using a first instance of the context map 308. In this aspect, the safety module 606 may close all the documents in the collection, if a discrepancy is identified between the first instance and a second instance of the context map 308.

In yet another aspect, the safety module 606 may inform the user of the discrepancy by generating a graphic indicator (not shown) for displaying on the user interface 714 and/or the patient data document. This indicator may be a symbol, icon, text notification, or message. Other indicators, such as audio signal or beep, may be used in some example embodiments.

In one aspect, the safety module 606 may determine if a discrepancy between the first and second instances of the context map 308 is material or significant. For example, the instances of the context map 308 may have different associated values for the context map property label of "Patient Home Address" yet have the same associated values for the context map property labels of "Patient ID," "Patient Last Name," and/or "Patient SSN." In this example, the discrepancy may be immaterial, as the patient data document and display are related to the same patient, although the patient may have moved to a new address. Thus, in some example embodiments, the safety module 606 may not automatically close the display of the patient data document. The safety module 606 may still inform the user of the discrepancy, such as by displaying a graphic and/or text indicator or generating an audio signal.

Figure 12:
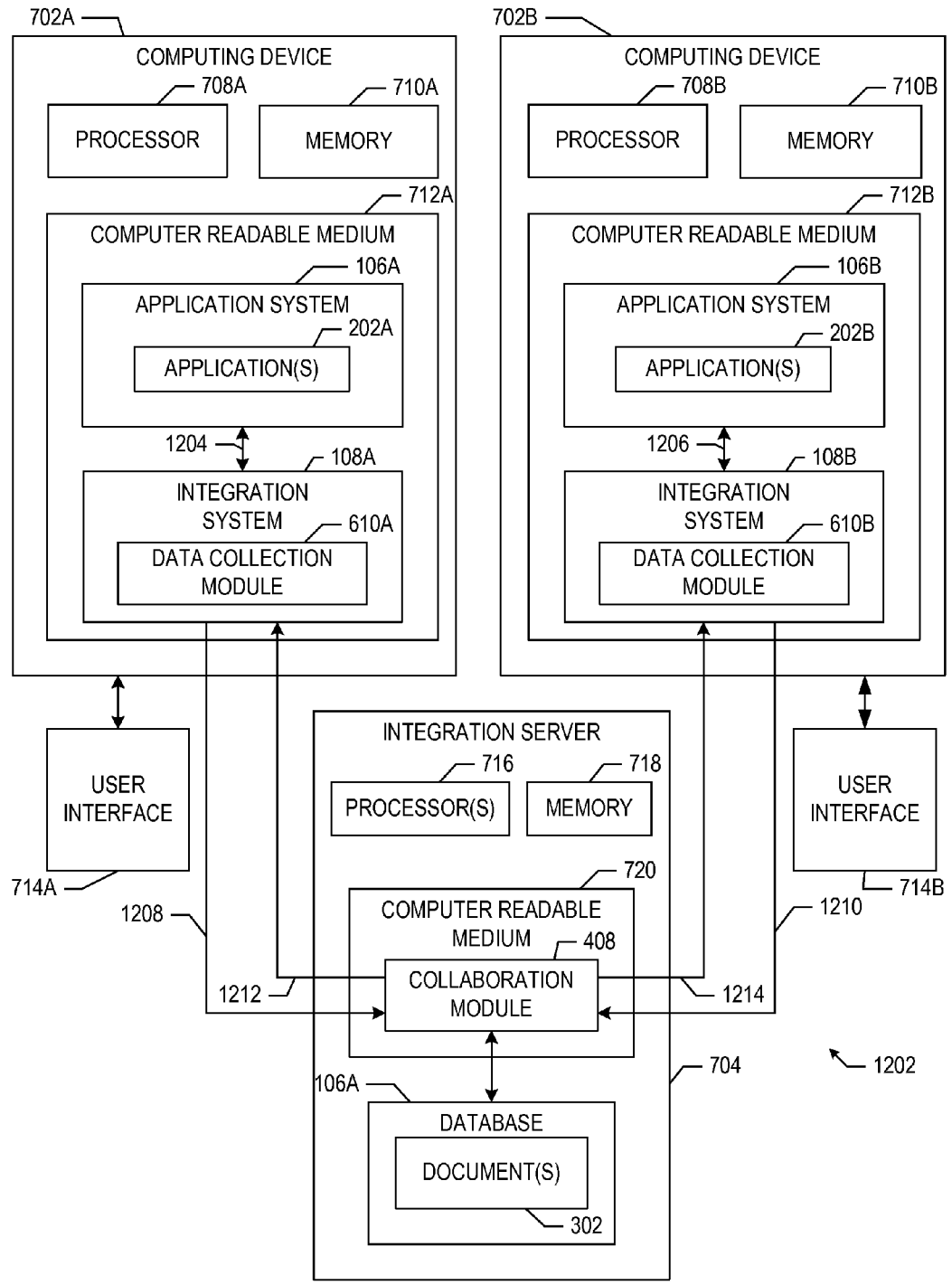
FIG. 12 is a block diagram of a collaboration notification function in accordance with one example embodiment of the integration system.

FIG. 12 is a block diagram depicting one example embodiment of a collaboration notification process 1202 as realized by the collaboration module 608 of the integration system 108A. For purposes of illustration, the modules 602-606 of the integration system 108A are not shown, and only the document 302 is shown within the database 106A of the integration server 704. While the application system 104A is shown to be part of the computing device 702 in FIG. 12, the application system may be external to the computing device.

In this example, the application integration system 102A may include one or more processing devices, such as the computing devices 702A, 702B, each executing the application 202A, 202B respectively. Each computing device 702A, 702B may also execute a respective integration system 108A, 108B.

The integration systems 108A and 108B may non-programmatically collect application data from the mapped locations of displays of the respective applications 202A, 202B, as indicated by 1204 and 1206. The application data may be collected from each display, the source references for the displays, and/or data may be collected from the operating system API for each application 202A, 202B. At the integration server 704, the collaboration module 608 compares the context map properties or the collected application data (without reference to the context map properties) for the displays of each application 202A, 202B, as indicated by 1208 and 1210.

The collaboration module 608 may determine if the collected application data collected from each application 202A, 202B is identical or otherwise corresponds to the same subject, event, and/or issue. For example, the collaboration module 608 may determine that the users of the computing devices 702A and 702B are viewing displays having context map properties that correspond to the same patient, even if the users are not viewing the same display or document. In this example, the displays may have the same collected application data as values for the same context map property. In another example, the collaboration module 608 may determine if one or more users are viewing information about the same event in a calendar application by comparing the context map properties for the displays viewed by the users.

If the collaboration module 608 determines that the context map properties for the display viewed by each user are identical or otherwise correspond to the same subject matter, the collaboration module 608 may notify, as indicated by 1212 and 1214, each user of the possibility for collaboration. For example, the collaboration module 608 may generate collaboration indicators for the user interfaces 714A, 714B in the form of pop-up messages, other messages, icons, and/or graphics or displays that may be displayed or otherwise rendered to each user. The collaboration indicators may include a message with collaboration information, such as the subject or subject matter of the collaboration. In some example embodiments, the collaboration indicators may include information about the one or more users that are or were viewing the same, similar, or related application data. In still other example embodiments, other indicators, such as audio signals in lieu of or in connection with visual indicators may be used.

In one aspect, the collaboration module 608 may enable or facilitate communication between the users of the computing devices 702A, 702B. For example, the collaboration module 608 may include an instant messaging function that allows the users to communicate in real time. In another example, the collaboration module 608 may include a non-real time messaging function, where the users may post messages to be read by future users that view application data having the same context map properties or otherwise having the same collected application data. In other example embodiments, the collaboration module 608 may direct users to another application for collaboration between users.

In another aspect, the collaboration module 608 may notify a user that one or more other users who have viewed identical or otherwise corresponding application data and/or documents have also viewed other application data and/or documents. For example, the collaboration module 608 may notify a first user who is viewing a particular patient data document for Patient A that a second user has also viewed the same patient data document and that the second user has also viewed one or more other patient data documents.

Figure 13:
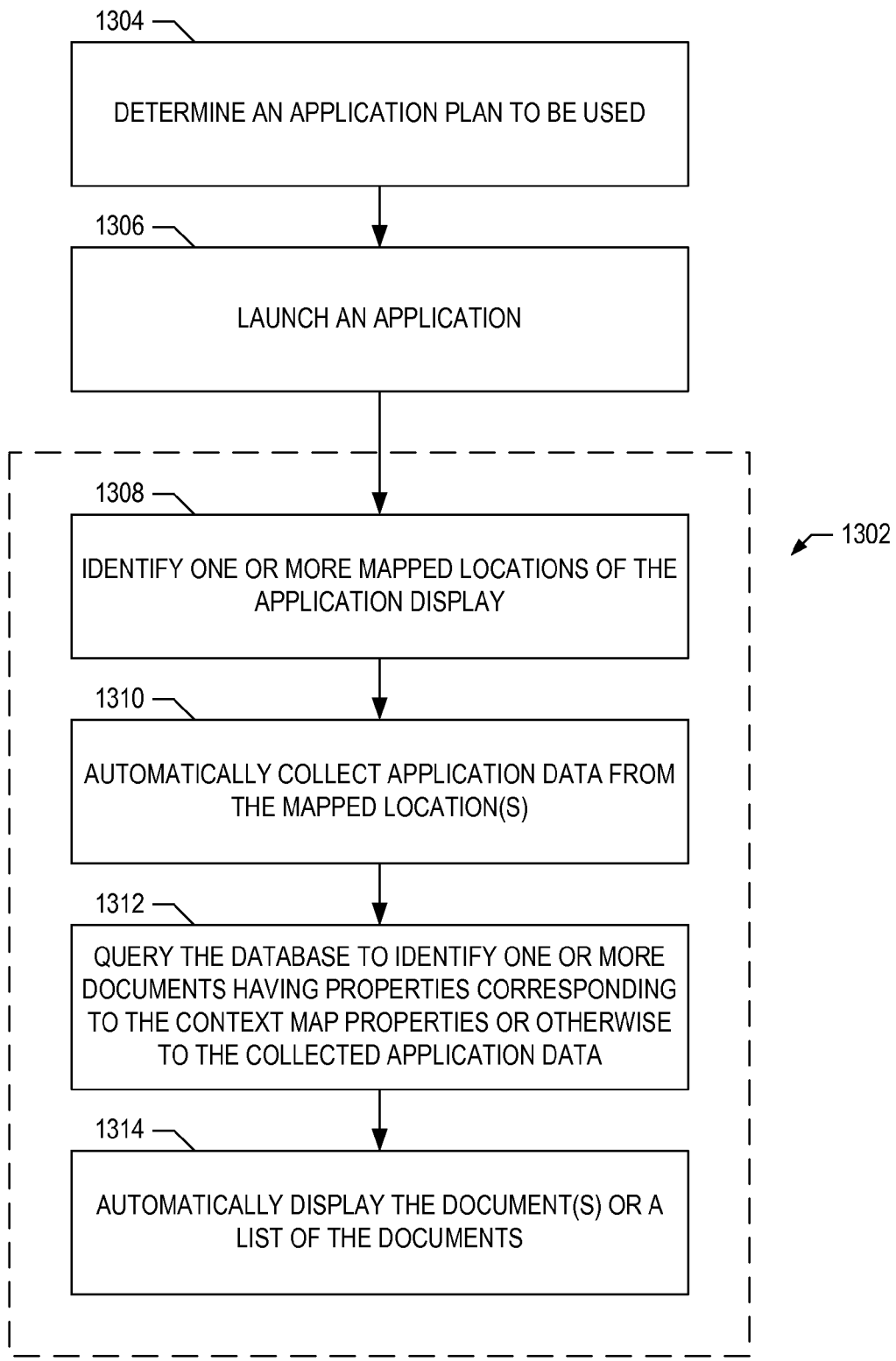
FIG. 13 is a flow diagram of a proactive notification process in accordance with one example embodiment of the application integration system.

FIG. 13 is a flowchart of a proactive notification process 1302 as performed by the notification module 602. As used herein, proactive refers to a query conducted automatically without being explicitly requested by the user. At block 1304, an application plan, such as the application plan 304, that corresponds to an application, such as the application 202, may be identified and selected before, while, or after the application is launched. The application plan 304 to be used may be identified based upon a configuration file for the computing device, the application executable files currently executing on the computing device, and/or a selection of an application plan made by the user.

At block 1306, the user may launch the application 202. In one aspect, the user may launch the application 202 before the application plan 304 is identified. In another aspect, the user may launch the application 202 while or after the application plan 304 is identified.

The notification module 602 may identify one or more mapped locations of an application display at block 1308. At block 1310, the notification module 602 may non-programmatically collect application data from the mapped locations. In some example embodiments, the data collection module 610 may perform steps block 1306 and block 1308.

At block 1312, the notification module 602 may query the database 106A to identify one or more documents, such as the document 302, whose properties match the context map properties or whose properties otherwise match the collected application data without reference to the context map. After identifying one or more documents that fit the query criteria, the notification module 602 may proactively display the matching documents or thumbnails of the documents. In some example embodiments, the notification module 602 may display a list of matching documents on a user interface for review by the user at 1314. In one aspect, a pre-determined maximum threshold for the number of matching document properties may limit the number of documents displayed by the notification module 602.

Figure 14:
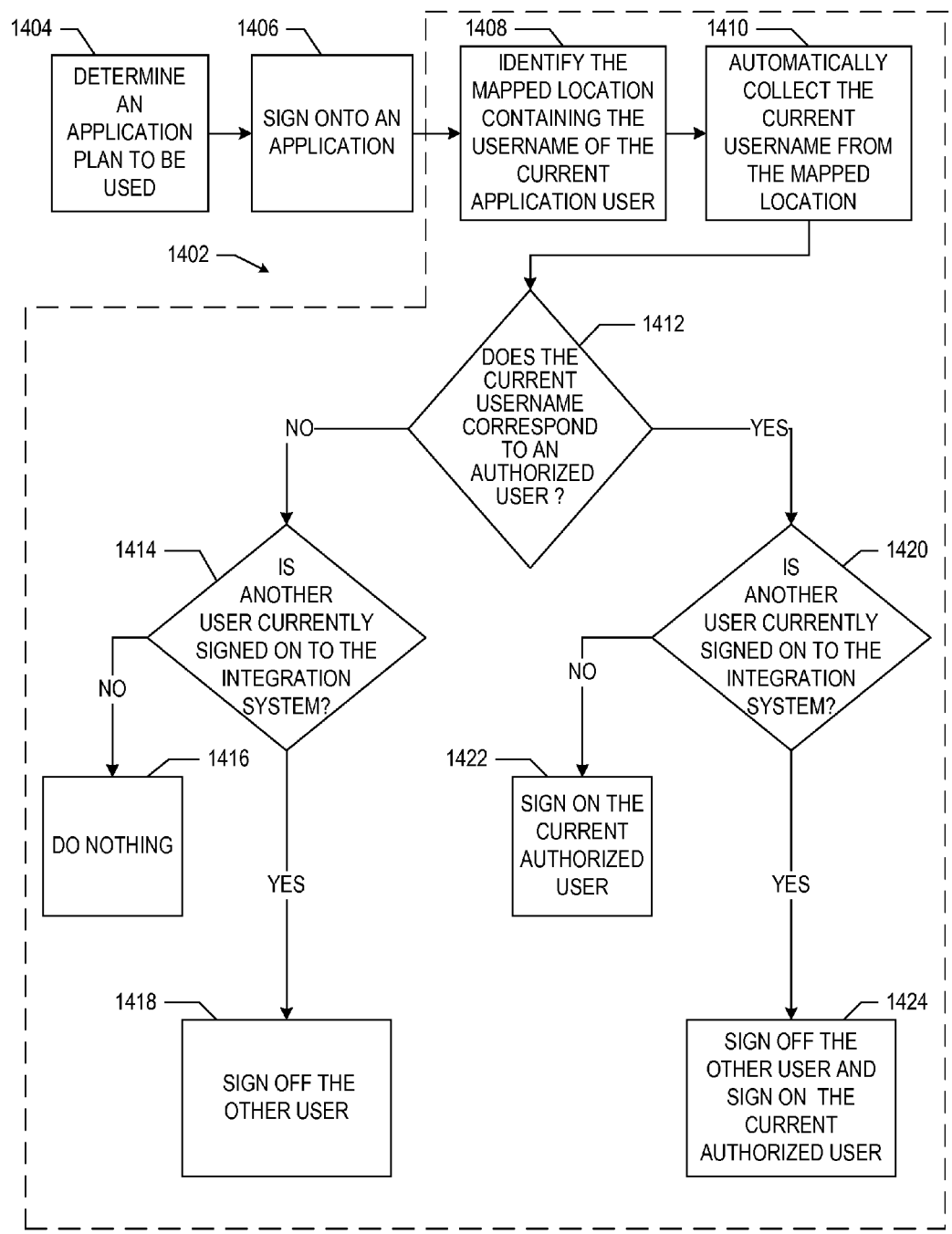
FIG. 14 is a flow diagram of an automatic sign-on/sign-off process in accordance with one example embodiment of the application integration system.

FIG. 14 is a flowchart of an automatic sign-on and sign-off process 1402 as performed by the synchronized sign-on module. At block 1404, an application plan, such as the application plan 304, that corresponds to an application, such as the application 202, may be identified and selected before, while, or after the application is launched. The application plan 304 to be used may be identified based upon a configuration file for the computing device, the application executable files currently executing on the computing device, and/or a selection of an application plan made by the user.

At block 1406, the user may sign on to the application 202 executing on a computing device. In some example embodiments, steps 1404 and 1406 may be reversed. At block 1408, the synchronized sign-on module 604 may identify the mapped location of a display generated by the application 202 that includes the user identifier or other information identifying the current user of the application.

At block 1410, the synchronized sign-on module 604 may non-programmatically, automatically, and continuously collect the application data from the identified mapped location containing the current user identifier. In some example embodiments, the data collection module 610 could perform steps 1408 and 1410.

At block 1412, the synchronized sign-on module 604 may determine if the user identifier for the user of the application 202 corresponds to an authorized user of the integration system 108A. If the user of the application 202 is not an authorized user of the integration system 108A, the synchronized sign-on module 604 may next determine if another user is currently signed on to the integration system at block 1414. If no other user is currently signed on to the integration system 108A, the synchronized sign-on module 604 does nothing at block 1416. If it is determined at block 1414 that another user is signed on, the synchronized sign-on module 604 may automatically sign off the other user signed on to the integration system 108A at block 1418 to prevent the user of the application 202 from accessing the features and functions of the integration system 108A.

If the determination at block 1412 is affirmative (i.e., the user of the application 202 is an authorized user of the integration system 108A), the synchronized sign-on module 604 may next determine at block 1420 if another user is currently signed on to the integration system. If the sign-on module 604 determines that no other user is signed on to the integration system 108A, the synchronized sign-on module 604 may automatically sign the user of the application 202 on to the integration system at block 1422. Similarly, if the synchronized sign-on module 604 determines that a different user is currently signed on to the integration system 108A at block 1420, the synchronized sign-on module 604 may sign the other user off of the integration system and automatically sign the user of the application 202 on to the integration system at block 1424.

In one aspect, if the user of the application 202 is signed on to the integration system 108A but subsequently signs out of the application 202 so that there is no application data for the synchronized sign-on module 604 to collect from the identified mapped location, the user of the application 202 may be automatically signed out of the integration system 108A.

Figure 15:
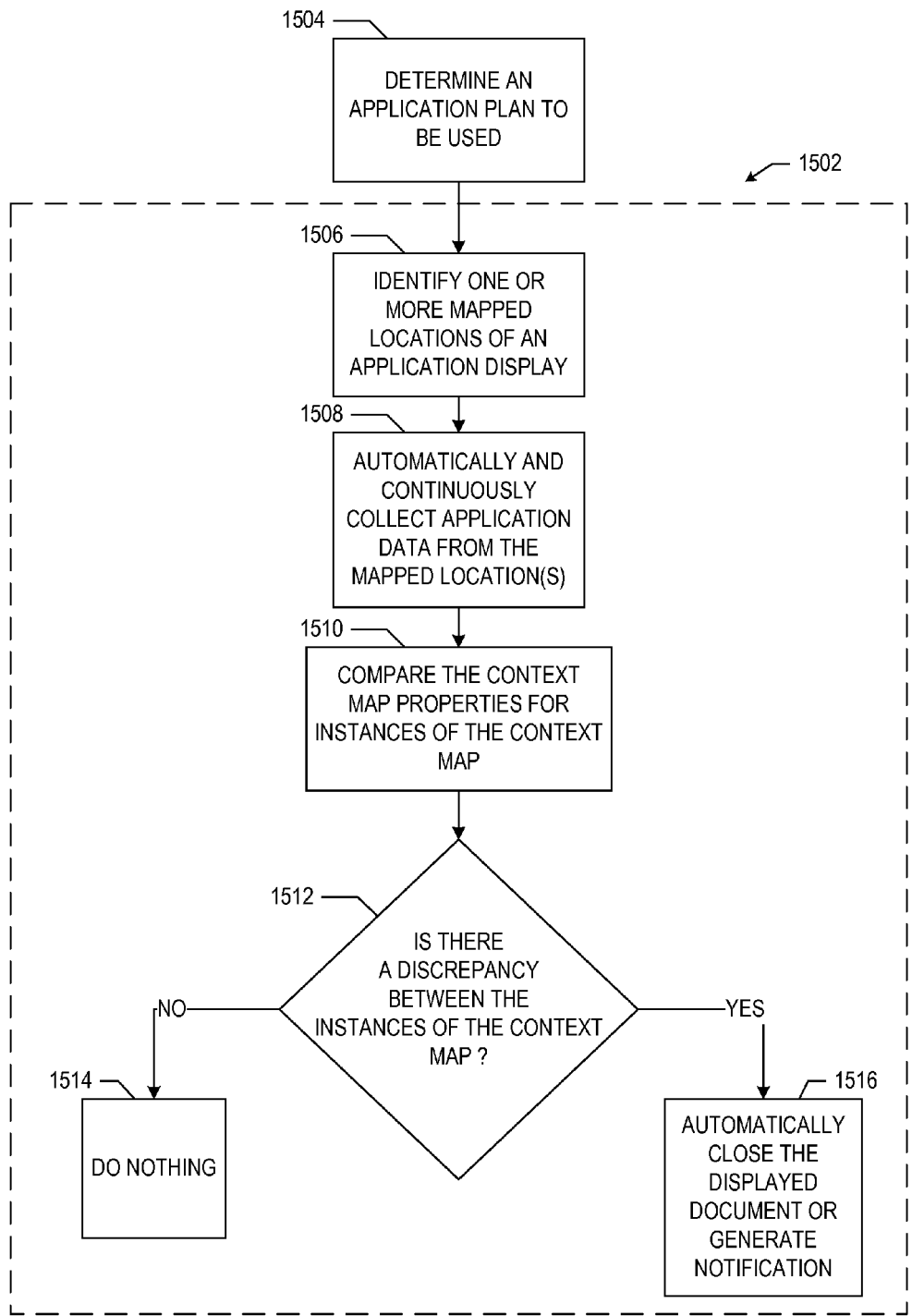
FIG. 15 is a flow diagram of a context safety process in accordance with one example embodiment of the application integration system.

FIG. 15 is a flowchart of a context safety process 1502 as performed by the safety module 606. At block 1504, an application plan, such as the application plan 304, that corresponds to an application, such as the application 202, may be identified and selected. The application plan 304 may be identified before, while, or after the application 202 is launched. The application plan 304 to be used may be identified based upon a configuration file for the computing device, the application executable files currently executing on the computing device, and/or a selection of an application plan made by the user.

At block 1506, the safety module 606 identifies one or more mapped locations of a display generated by an application, such as the application 202. At block 1508, the safety module 606 may non-programmatically, automatically, and continuously collect application data from one or more mapped locations to generate a first instance of the context map 308 that is used to identify and retrieve a document, such as the document 302. The safety module 606 may continue to collect application data from one or more mapped locations to generate a second instance of the context map 308. In some example embodiments, the data collection module 610 may perform steps 1506 and/or 1508.

At block 1510, the safety module 606 may compare the context map properties for a first instance of the context map 308, used to identify and retrieve the document 302, with the second instance of the context map. The safety module 606 may determine if a discrepancy exists between the first instance and the second instance of the context map 308. If a discrepancy is not identified at block 1512, then the safety module 606 may do nothing at block 1514. If a discrepancy is identified by the safety module 606 at block 1512, then the safety module 606 may automatically close the display of the document 302 at block 1516. In some example embodiments, the safety module 606 may notify the user of the discrepancy in lieu of or in addition to closing the display of document 302. For example, the integration system 108 may generate an audio signal and/or a visual indicator in conjunction with or as an alternative to closing the display of the document 302. In some example embodiments, the safety module 606 may prompt the user for action.

Figure 16:
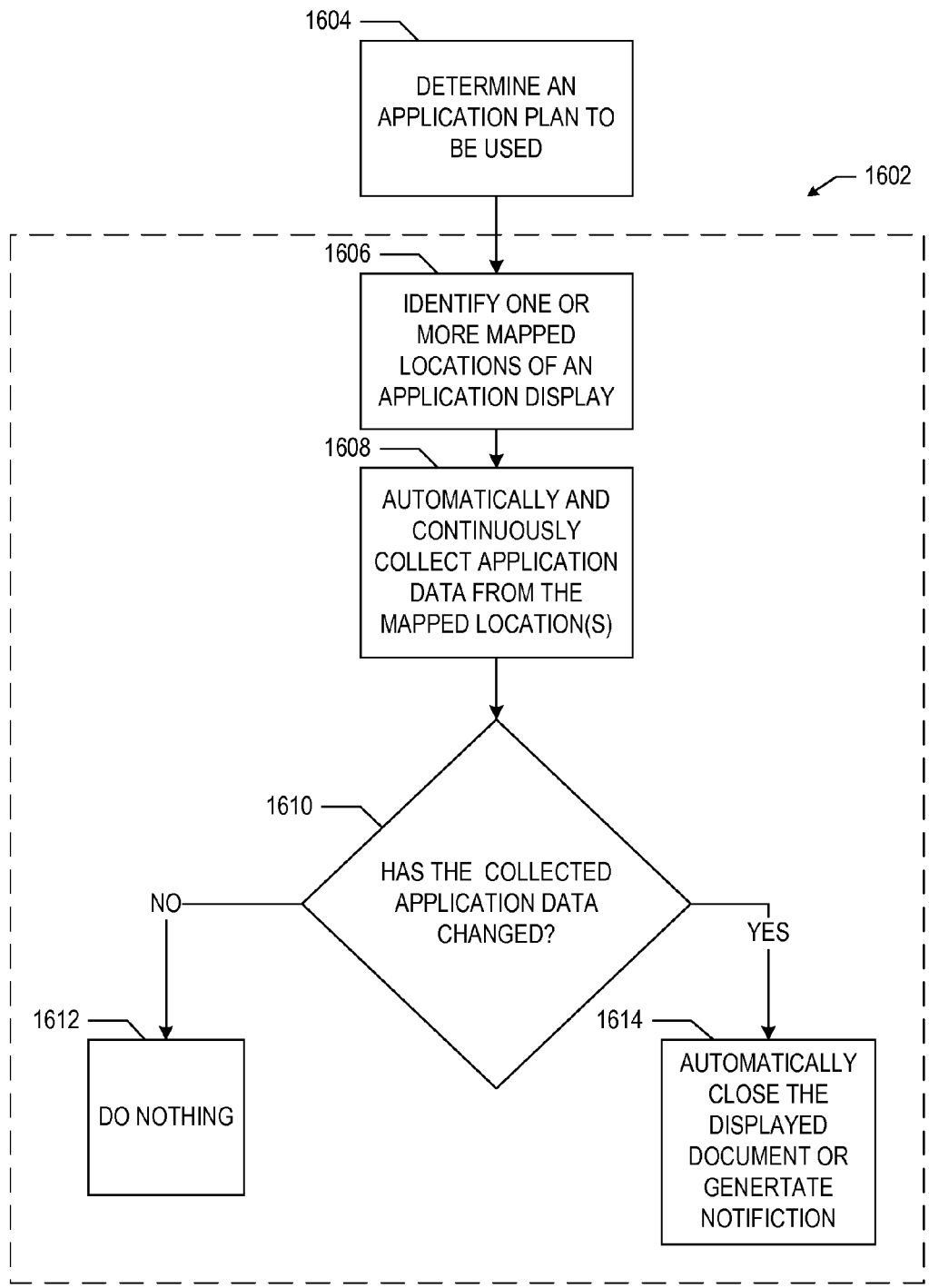
FIG. 16 is a flow diagram of another context safety process in accordance with one example embodiment of the application integration system.

FIG. 16 is a flowchart of another context safety process 1602 as performed by the safety module 606. At block 1604, an application plan, such as the application plan 304, that corresponds to an application, such as the application 202, may be identified and selected. The application plan 304 to be used may be identified based upon a configuration file for the computing device, the application executable files currently executing on the computing device, and/or a selection of an application plan made by the user.

At block 1606, the safety module 606 may identify one or more mapped locations of a display generated by an application, such as the application 202. At block 1608, the safety module 606 may non-programmatically, automatically, and continuously collect application data from one or more mapped locations. In one aspect, the collected application data may be used to populate an instance of the dictionary 306 and/or the context map 308. The safety module 606 may continue to collect application data from one or more mapped locations. In some example embodiments, the data collection module 610 may performs steps 1606 and/or 1608.

At block 1610, the safety module 606 may determine if the collected application data has changed at one or more mapped locations. In one aspect, the safety module 606 may compare current collected application data to the collected application data in an instance of the dictionary 306. In another aspect, the safety module 606 may compare current collected application data to the collected application data in an instance of the context map 308.

In yet another aspect, the safety module 606 may compare collected application data in an instance of the dictionary 306 to the collected application data in an instance of the context map 308. In still another aspect, the safety module 606 may compare collected application data and the dictionary labels in an instance of the dictionary 306 to the collected application data and the labels in the instance of the context map 308. In yet another aspect, the safety module 606 may compare current collected application data to the collected application of another data structure and/or the labels for another data structure.

If a change is not identified at block 1610, then the safety module 606 does nothing (block 1612). If any change to the application data collected from one or more mapped locations is identified by the safety module 606 at block 1610, then the safety module 606 may automatically close the display of the document 302 at block 1614 and/or notify the user of the discrepancy. In one aspect, the integration system 108 may generate an audio signal and/or a visual indicator in conjunction with or as an alternative to closing the display of the document 302. In another aspect, the notification may include prompting for additional user input.

Figure 17:
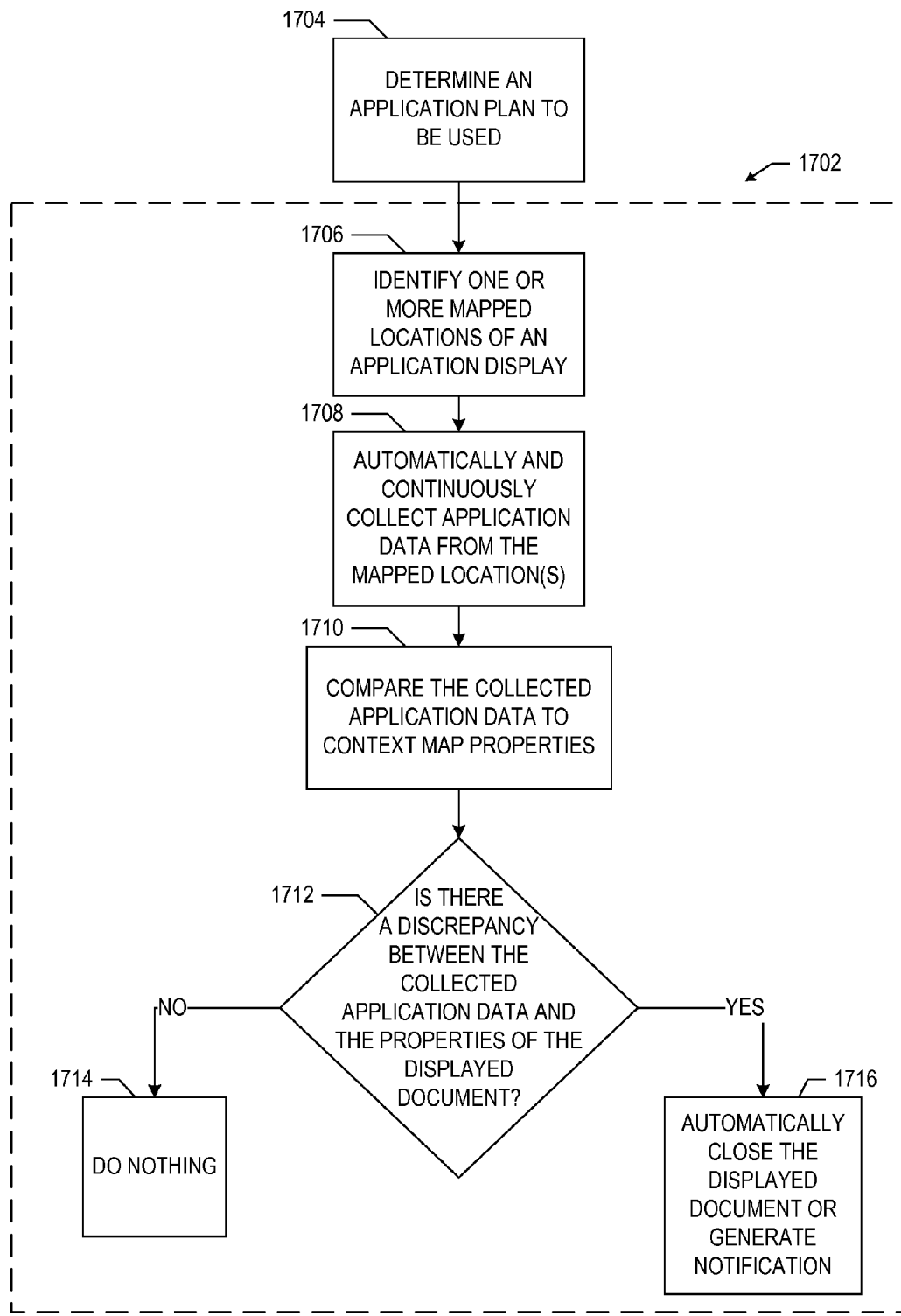
FIG. 17 is a flow diagram of another context safety process in accordance with one example embodiment of the application integration system.

FIG. 17 is a flowchart of a context safety process 1702 as performed by the safety module 606. At block 1704, an application plan, such as the application plan 304, that corresponds to an application, such as the application 202, is identified and selected before, while, or after the application 202 is launched. The application plan 304 used may be identified based upon a configuration file for the computing device, the application executable files currently executing on the computing device, and/or a selection an application plan made by the user.

At block 1706, the safety module 606 may identify one or more mapped locations of a display generated by an application, such as the application 202. At block 1708, the safety module 606 may non-programmatically, automatically, and continuously collect application data from one or more mapped locations to generate an instance of the context map 308 that is used to identify and retrieve a document, such as the document 302, for display. The safety module 606 may continue to collect application data from one or more mapped locations. In some example embodiments, the data collection module 610 may perform steps 1706 and/or 1708.

At block 1710, the safety module 606 may compare the current collected application data to the properties of the displayed document 302. The safety module 606 may determine if a discrepancy exists between the current collected application data and the properties of the displayed document 302. If a discrepancy is not identified at block 1712, then the safety module 606 may do nothing (block 1714). If a discrepancy is identified by the safety module 606 at block 1712, then the safety module 606 may automatically close the display of the document 302 (block 1716) and/or notify the user of the discrepancy. In one aspect, the integration system 108 may generate an audio signal and/or a visual indicator in conjunction with or as an alternative to closing the display of the document 302. In another aspect, notification may include prompting a user for a response or action.

Figure 18:
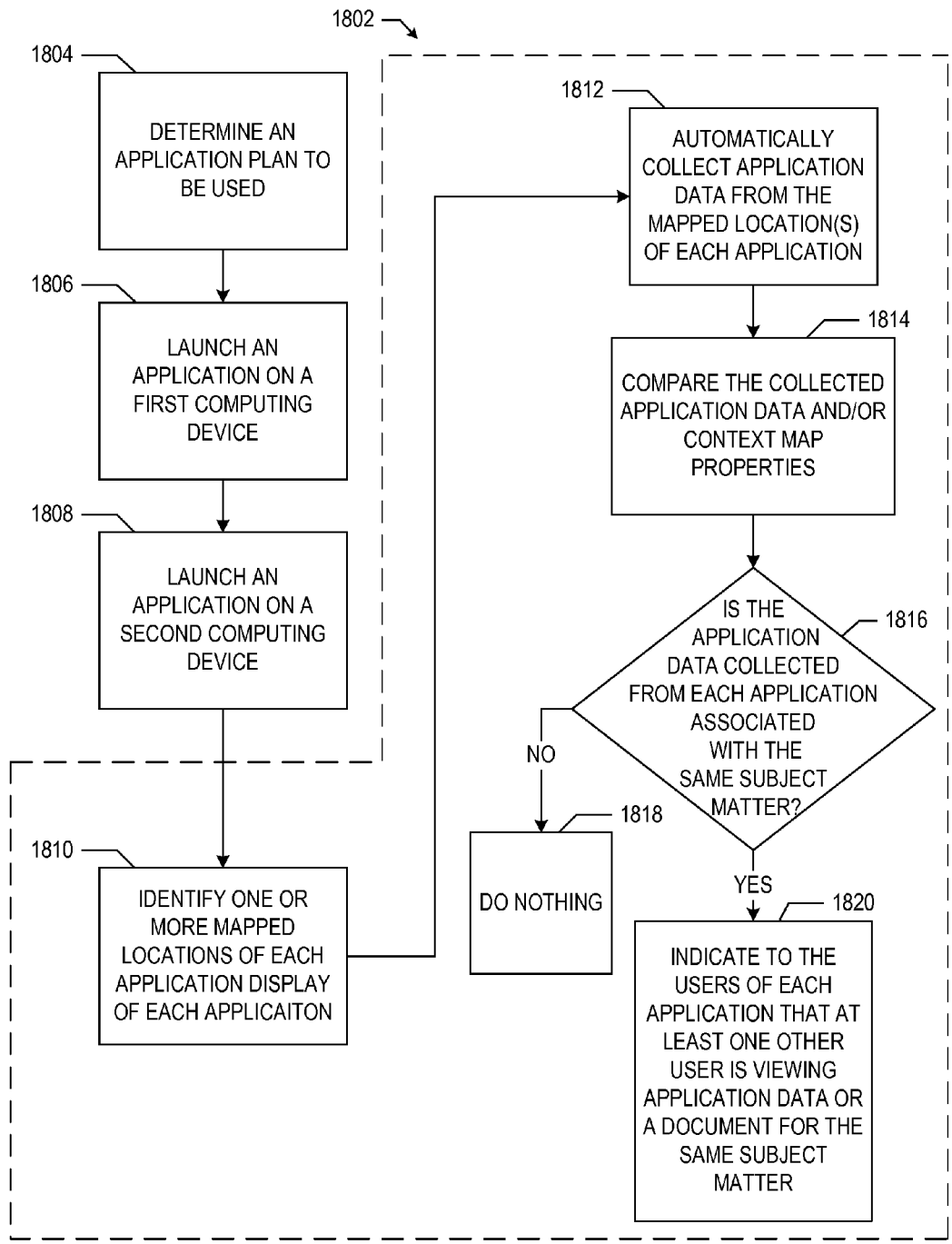
FIG. 18 is a flow diagram of a collaboration notification process in accordance with one example embodiment of the application integration system.

FIG. 18 is a flowchart of a collaboration notification process 1802 as performed by the collaboration module 608. At block 1804, two or more application plans, such as the application plan 304, that corresponds to an application, such as the applications 202A, 202B, may be identified and selected before, while, or after the application 202 is launched. The application plan 304 used may be identified based upon a configuration file for the computing device, the application executable files currently executing on the computing device, and/or a selection of an application plan made by the user. In some example embodiments, the criteria used for such determination may be preset or predetermined by a system administrator or user. In some other example embodiments, the criteria may be determined non-programmatically.

At block 1806, the application 202A may be launched on a first computing device 702A, and another instance of the application 202B may be launched on a second computing device 702B (block 1808). In other example embodiments, the computing devices 702A and 702B execute different applications. It will be appreciated by those skilled in the art that steps 1804-1808 may be performed in any order.

At block 1810, the integration systems 108A, 108B executing on each computing device 702A, 702B respectively, may identify one or more mapped locations in displays of each respective application 202A, 202B. The integration systems 108A, 108B may non-programmatically automatically collect application data from the mapped locations of the displays of the applications 202A, 202B at block 1812. In one aspect, the integration systems 108A, 108B may also identify the properties of any displayed documents. In some example embodiments, the data collection modules 802 for each integration system 108A, 108B may perform steps 1810 and/or 1812.

At block 1814, the collaboration module 608 may compare the context map properties or the collected application data without reference to the context map for each application 202A, 202B. The collaboration module 608 may determine if the context map properties or the collected application data are directed towards the same subject, event, and/or issue by comparing the context map properties or the collected application data for the displays of each respective application 202A, 202B at block 1816.

If the determination made at block 1816 is negative (i.e., the context map properties or collected application data viewed by the different users are not the same, similar or related), then the collaboration module 608 does nothing (block 1818). If the determination made at block 1816 is affirmative, then the collaboration module 608 may notify each user of the computing devices 702A, 702B that they are viewing application data or documents that are the same, similar, and/or related to application data, context map properties, and/or properties of documents as those being viewed by another user at block 1820.

The foregoing description of an embodiment has been presented for purposes of illustration. It is not intended to be exhaustive or to limit the application to the precise forms disclosed, and obviously many modifications and variations are possible in light of the above teaching. It is understood that the disclosure may be practiced in ways other than as specifically set forth herein without departing from the scope of the disclosure. It is intended that the scope of the application be defined by the claims appended hereto.

The invention claimed is:
1. A method of collaboration, comprising:
enabling a user to spatially define one or more mapped locations;

automatically non-programmatically collecting application data identifying a current user of an application from a mapped location of the application and automatically signing the current user on to an integration system as the current user of the integration system, wherein in response to a lack of application data in the mapped location of the application, signing a current user out of the integration system;

automatically non-programmatically collecting application data from a first mapped location of a mapped source reference of a first document when the current user accesses the first document through an application used by the current user;

when a second user accesses a second document through an application used by the second user while the current user is accessing the first document, automatically non-programmatically collecting application data from a second mapped location of a mapped source reference of the second document;

determining whether the collected application data from the first mapped location matches the collected application data from the second mapped location; and when the first collected application data matches the second collected application data, automatically notifying at least one of the current user and second user that the at least one of the current and second users are accessing associated documents, wherein the first and the second documents are indexed by populating document properties for the first and the second documents using the collected application data.

2. The method of claim 1, wherein the notifying comprises providing collaboration information.

3. The method of claim 2, wherein the collaboration information comprises a universal resource locator of a collaboration tool.

4. The method of claim 2, wherein the collaboration information comprises contact information associated with the users.

5. The method of claim 1, further comprising automatically commencing a collaboration tool when the first collected application data matches the second collected application data.

6. The method of claim 5, wherein the collaboration tool is a software application.

7. The method of claim 5, wherein the collaboration tool is an instant messaging application.

8. The method of claim 1, wherein the notifying comprises displaying a visual indicator.

9. The method of claim 1, wherein the notifying comprises playing an audio signal.

10. The method of claim 1, wherein the notifying comprises sending an electronic mail message.

11. The method of claim 1, wherein the determining continuously compares the collected application data from the first mapped location with the collected application data from the second mapped location while the users are accessing the associated documents.

12. The method of claim 1, wherein the determining compares the collected application data from the first mapped location with the collected application data from the second mapped location at a predetermined interval.

13. The method of claim 1, wherein the collected application data from the first mapped location matches the collected application data from the second mapped location if the collected application data from the first mapped location is associated with the collected application data from the second mapped location.

14. The method of claim 1, wherein the collected application data from the first mapped location matches the collected application data from the second mapped location if the collected application data from the first mapped location is substantially the same as the collected application data from the second mapped location.

15. The method of claim 1, wherein if the collected application data from the first mapped location matches the collected application data from the second mapped location, the first and the second users are accessing identical documents in the database.

16. A method of collaboration, comprising:
enabling a user to spatially define one or more mapped locations;

automatically non-programmatically collecting application data identifying a current user of an application from a mapped location of the application and automatically signing the current user on to an integration system as the current user of the integration system, wherein in response to a lack of application data in the mapped location of the application, signing a current user out of the integration system;

automatically non-programmatically collecting application data from a first mapped location of a mapped first document accessed in an application by the current user;

when a second user accesses a mapped second document through another application used by the second user while the current user is accessing the first document, determining whether the collected application data from the first mapped location matches previously collected application data from a second mapped location of the mapped second document being accessed by the second user; and when the first collected application data matches the previously collected application data, automatically notifying at least one of the current user and the second user that at least one of the current and the second users are accessing associated documents, wherein the first and the second documents are indexed by populating document properties for the first and the second documents using the collected application data.

17. The method of claim 12, wherein the determining is continuously performed while the first and second users are accessing the first and second documents, respectively.

18. The method of claim 16, wherein the determining occurs at a predetermined interval.

19. A collaboration system, comprising at least one module executing on at least one processor to:
enable a user to spatially define one or more mapped locations;

automatically non-programmatically collect application data identifying a current user of an application from a mapped location of the application and automatically sign the current user on to an integration system as the current user of the integration system, wherein in response to a lack of application data in the mapped location of the application, sign a current user out of the integration system;

automatically non-programmatically collect application data from a first mapped location of a first document accessed through an application used by the current user;

when a second user accesses a second document through another application used by the second user while the current user is accessing the first document, automatically non-programmatically collect application data from a second mapped location of the second document;
determine whether the collected application data from the first mapped location matches the collected application data from the second mapped location; and
when the first collected application data matches the second collected application data, automatically notify at least one of the current user and second user that the current and the second users are accessing associated documents,
wherein the first and the second documents are indexed by populating document properties for the first and the second documents using the collected application data.

20. The collaboration system of claim 19, wherein the determining whether the collected application data from the first mapped location matches the collected application data from the second mapped location occurs in a second module executing on a second processor.

* * * * *